(12) United States Patent
Miasnikov et al.

(10) Patent No.: US 8,143,045 B2
(45) Date of Patent: Mar. 27, 2012

(54) **MUTANT *CITROBACTER FREUNDII* PHYTASE POLYPEPTIDE**

(75) Inventors: Andrei Miasnikov, Degerby (FI); Vijay Kumar, Casnate (IT); Oliver Kensch, Cologne (DE); Klaus Pellangahr, Cologne (DE); Birgitta Leuthner, Cologne (DE); Ulrich Kettling, Cologne (DE); Andre Koltermann, Köln (DE)

(73) Assignee: Danisco A/S, Copenhagen (DK)

( * ) Notice: Subject to any disclaimer, the term of this patent is extended or adjusted under 35 U.S.C. 154(b) by 278 days.

(21) Appl. No.: 11/696,162

(22) Filed: Apr. 3, 2007

(65) Prior Publication Data

US 2009/0074925 A1    Mar. 19, 2009

Related U.S. Application Data

(63) Continuation-in-part of application No. PCT/IB2005/003660, filed on Oct. 4, 2005.

(51) Int. Cl.
*C12N 9/16* (2006.01)
*C12Q 1/44* (2006.01)

(52) U.S. Cl. ........ 435/196; 435/19; 435/183; 424/94.61
(58) Field of Classification Search ........................ None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,939,352 A | 2/1976 | Mester et al. | |
| 3,996,345 A | 12/1976 | Ullman et al. | |
| 4,275,149 A | 6/1981 | Litman et al. | |
| 4,277,437 A | 7/1981 | Maggio et al. | |
| 4,366,241 A | 12/1982 | Tom et al. | |
| 4,683,202 A | 7/1987 | Mullis et al. | |
| 4,816,567 A | 3/1989 | Cabilly et al. | |
| 4,946,779 A | 8/1990 | Kameda et al. | |
| 5,605,793 A | 2/1997 | Stemmer et al. | |
| 5,674,707 A | 10/1997 | Hintz et al. | |
| 5,723,323 A | 3/1998 | Kauffman et al. | |
| 5,741,665 A | 4/1998 | Kato et al. | |
| 6,132,970 A | 10/2000 | Stemmer et al. | |
| 6,303,344 B1 | 10/2001 | Patten et al. | |
| 6,821,758 B1 | 11/2004 | Koltermann et al. | |

FOREIGN PATENT DOCUMENTS

| EP | 0238023 | 10/2002 |
|---|---|---|
| EP | 1392353 | 3/2004 |
| EP | 1230390 | 9/2004 |
| EP | 0449375 A | 5/2006 |
| EP | 1389915 | 9/2007 |
| JP | 2002-507412 | 3/2002 |
| KR | 10-2004-0045267 | 6/2004 |
| WO | WO9117243 | 11/1991 |
| WO | WO9218645 | 10/1992 |
| WO | WO 98/06856 | 2/1998 |
| WO | WO 99/49022 | 9/1999 |
| WO | WO0058517 | 10/2000 |
| WO | WO0134835 | 5/2001 |
| WO | WO02097130 | 12/2002 |
| WO | WO03012100 | 2/2003 |
| WO | WO 03/037102 | 5/2003 |
| WO | WO03057247 | 7/2003 |
| WO | WO 03/102174 | 12/2003 |
| WO | WO2004018674 | 3/2004 |
| WO | WO 03/038111 | 4/2006 |
| WO | WO 2006/037327 | 4/2006 |
| WO | WO 2006/037328 | 4/2006 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Kim et al., Biotechnol. Lett. vol. 28, pp. 33-38, 2006.*
H. Guo et al., "Protein Tolerance to Random Amino Acid Change", PNAS 101(25): 9205-9210, Jun. 2004.*
Han-Woo Kim, et al., Isolation and Characterization of a Phytase With Improved Properties From *Citrobacter braakii*, Biotechnology Letters (2003) vol. 25, p. 1231-1234.
Zinin, N.V., et al., Phytase Activity of Several Bacteria Groups, Biotehnologi, Moscow, SU, No. 2 (2003) p. 3-10 (Abstract).
Randy M. Berka, et al., Molecular Characterization and Expression of a Phytase Gene From the Thermophilic Fungus *Thermomcyes lanuginosus*, Applied and Environmental Microbiology (1998) vol. 64, No. 1, p. 4423-4427.
R. Greiner, et al., Purification and Characterization of Two Phytases From *Escherichia coli*, Archives of Biochemistry and Biophysics (1993) vol. 303, No. 1, p. 107-113.
R. Greiner, et al., Purification and Characterization of a Phytase From *Klebsiella terrigena*, Archives of Biochemistry and Biophysics (1997) vol. 341, No. 2, p. 201-206.
F.A. Igbasan, et al., Comparative Studies on the In Vitro Properties of Phytases From Various Microbial Origins, Arch. Anim. Nutr (2000) vol. 53, p. 353-373.
Janne Kerovuo, et al., Isolation, Characterization, Molecular Gene Cloning, and Sequencing of a Novel Phytase From *Bacillus subtilis*, Applied Environmental Microbiology (1998) vol. 64, No. 6, p. 2079-2085.
Janne Kerovuo, et al, Analysis of Myo-Inositol Hexakisphosphate Hydrolysis by Bacillus Phytase: Indication of a Novel Reaction Mechanism, Biochem. J. (2000) vol. 352, p. 623-628.
Soren F. Lassen, et al., Expression, Gene Cloning, and Characterization of Five Novel Phytases From Four Basidiomycete Fungi: *Peniophora lycii, Agrocybe pediades, A ceriporia* sp., and *Trametes pubescens*, Applied Environmental Microbiology (2001) vol. 67, No. 10, p. 4701-4707.

(Continued)

*Primary Examiner* — Richard Hutson
(74) *Attorney, Agent, or Firm* — Steptoe & Johnson LLP

(57) ABSTRACT

The present invention relates to enzymes and processes. In particular, there is described an isolated polypeptide comprising the amino acid sequence corresponding to *Citrobacter freundii* phytase or a homologue, a modified form, a functional equivalent or an effective fragment thereof. There is also described a host cell transformed or transfected with a nucleic acid encoding a bacterial phytase enzyme or a modified form as well as the use of such a phytase or modified form in food or animal feed.

10 Claims, 2 Drawing Sheets

OTHER PUBLICATIONS

U. Schlemmer, et al., Degradation of Phytate in the Gut of Pigs—Pathway of Gastrointestinal Inositol Phosphate Hydrolysis and Enzymes Involved, Arch. Anim. Nutr. (2001) vol. 55, pl. 255-280.
Markus Wyss, et al., Biochemical Characterization of Fungal Phytases (myo-Inositol Hexakisphosphate Phosphohydrolases): Catalytic Properties, Applied Environmental Microbiology (1999) vol. 65, No. 2, p. 367-373.
Seong Jun Yoon, et al., Isolation and Identification of Phytase-Producing Bacterium, *Enterobacter* sp. 4, and Enzymatic Properties of Phytase Enzyme, Enzyme and Microbial Technology (1996) vol. 18, 449-454.
Nickolay Zinin, et al., Gene Cloning, Expression and Characterization of Novel Phytase From *Obesumbacterium proteus*, FEMS Microbiology Letters (2004) vol. 236, p. 283-290.
Altschul, S. et. al. (1990). Basic Local Alignment Search Tool. Journal of Molecular Biology, vol. 215, p. 403-410.
Archer, D. et. al. (1997). The molecular biology of secreted enzyme production by fungi. Critical Reviews in Biotechnology, vol. 17, No. 4, p. 273-306.
Ausubel, F. et. al. (1999). Sequence Similarity Searching Using the BLAST Family of Programs. Short Protocols in Molecular Biology, Fourth Edition, Chapter 18, p. 18-01-18-23.
Ausubel, F. et. al. (1999). Homology Searching. Short Protocols in Molecular Biology, Fourth Edition, Chapter 7, p. 7-58-7-60.
Beaucage, S.L., et. al. (1981). Deoxynucleoside Phosphoramites—A New Class of Key Intermediates for Deoxypolynucleotide Synthesis. Tetrahedron Letters, vol. 22, No. 20, pp. 1859-1869.
Beggs, J. (1978). Transformation of yeast by a replicating hybrid plamid. Nature, vol. 275, p. 104-109.
Bessette, P. et. al. (1999). Efficient Folding of Proteins with multiple Disulfide Bonds in the *Escherichia coli* cytoplasm. Department of Chemical Engineering and Institute for Cell and Molecular Biology, University of Texas, vol. 96, No. 24, p. 13703-13708.
Caruthers, M. H. et. al. (1980). New Chemical Methods for Synthesizing Polynucleotides. Nucleic Acids Research, Symposium Series, No. 7, p. 215-223.
Cereghino, J. et. al. (2000). Heterologous Protein Expression in the Methylotrophic Yeast *Pichia pastoris*. FEMS Microbiology Reviews, vol. 24, p. 45-66.
Christou, P. (1994). Genetic Engineering of Crop Legumes and Cereals: Current Status and Recent Advances. Agro-Food-Industry Hi-Tech, Mar./Apr. 1994, p. 17-27.
Cole, S.P.C. (1985). The Ebv-Hyberidoma Technique and Its Application to Human Lung Cancer. Monoclonal Antibodies and Cancer Therapy, p. 77-96.
Cote, R. (1983). Generation of Human Monoclonal Antibodies Reactive with Cellular Antigens. Immunology, vol. 80, p. 2026-2030.
Davis, R. et. al. (1971). Genetic and Microbiological Research Techniques for *Neurospora crassa*. Microbiological Techniques, vol. 17A, p. 79-143.
Devereux, J. et. al. (1984) A Comprehensive Set of Sequence Analysis Programs for the VAX. Nucleic Acids Research, vol. 12, No. 12, p. 387-395.
Heinonen, J. et. al. (1981). A new and convenient colorimetric determination of inorganic orthophosphate and its application to the assay of inorganic pyrophosphatase. Analytical Biochemistry, vol. 113, No. 2, p. 313-317.
Higgins, D. et. al. (1988). Clustal: a Package for Performing Multiple Sequence Alignment on a Microcomputer. Gene, vol. 73, p. 237-244.
Hinchcliffe, E. et. al. (1993). Yeasts as a Vehicle for the Expression of Heterologous Genes. The Yeasts, vol. 5, $2^{nd}$ Edition, p. 325-356.
Hinnan, A., et. al. (1978). Transformation of yeast. Proceedings of the National Academy of Sciences of the USA, vol. 75, p. 1929-1933.
Holland, B. et. al. (1990). Secretion of heterologous proteins in *Escherichia coli*. Methods in Enzymology, vol. 182, p. 132-143.
Hollenberg, C. et. al. (1997). Production of recombinant proteins be methylotrophic yeasts. Current Opinions in Biotechnology, vol. 8, No. 5, p. 554-560.
Horn, T. et. al. (1980). Synthesis of oligonucleotides on cellulose. Part II: design and synthetic strategy to the synthesis of 22 oligodeoxynucleotides coding for Gastric Inhibitory Polypeptide (GIP). Nucleic Acids Research, Symposium Series, No. 7, p. 225-232.
Hornwell, D. (1995). The 'peptoid' approach to the design of non-peptide, small molecule agonists and antagonists of neuropeptides. Trends in Biotechnology, vol. 13, No. 4, p. 132-134.
Howson, S. J. et. al. (1983). Production of phytate-hydrolysing enzyme by some fungi. Enzyme Microbiology Technology, vol. 5, p. 377-382.
Huse, W. et. al. (1989). Generation of a large combinatorial library of the immunoglobulin repertoire in phage lambda. Science, vol. 256, p. 1275-1281.
Ito, H. et. al. (1983). Transformation of Intact yeast cells treated with alkali cations. Journal of Bacteriology, vol. 153, No. 1, p. 163-168.
Kane, J. (1995). Effects of rare codon clusters on high-level expression of heterologous proteins in *Escherichia coli*. Current Opinion in Biotechnology, vol. 6, No. 5, p. 494-500.
Kim, H. et. al. (2003). Isolation and characterization of a phytase with improved properties from *Citrobacter braakii*. Biotechnology Letters, vol. 25, p. 1231-1234.
Koehler, G. et. al. (1975). Continuous cultures of fused cells secreting antibody of predefined specificity. Nature, vol. 256, p. 495-497.
Kozbor, D. et. al. (1983). The production of monoclonal antibodies from human lymphocytes. Immunology Today, vol. 4, No. 3, p. 72-79.
Lane, D. (1991). 16S/23S rRNA Sequencing. Nucleic Acid Techniques in Bacterial Systematics, edited by Stackbrant, E. and Goodfellow, M., John Wiley and Sons, Ltd, p. 115-175.
Lavillie, E. et. al. (1995). Gene fusion expression systems in *Escherichia coli*. Current Opinion in Biotechnology, vol. 6, No. 5, p. 501-506.
Livingstone, C. et. al. (1993). Protein sequence alignments: a strategy for the hierarchical analysis of residue conservation. Computer Application Bioscience, vol. 9, p. 745-756.
Matthes, H. et.al. (1984). Simultaneous rapid chemical synthesis of over one hundred oligonucleotides on a microscale. The EMBO Journal, vol. 3, No. 4, p. 801-805.
Morinaga, Y. et. al. (1984). Improvement of oligonucleotide-directed site-specific mutagenesis using double-stranded plasmid DNA. Biotechnology, vol. 2, p. 646-649.
Morrison, S. et. al. (1984). Chimeric human antibody molecules: Mouse antigen-binding domains with human constant region domains. Proc. Natl. Acad. Sci. USA, Immunology, vol. 81, p. 6851-6855.
Nelson, R. et. al. (1989). A general method of site-specific mutagenesis using a modification of the *Thermus aquaticus* polymerase chain reaction. Analytical Biochemistry, vol. 180, p. 147-151.
Neuberger, M. et. al. (1984). Recombinant antibodies possessing novel effector functions. Nature, vol. 312, p. 604-608.
Potrykus, I. (1991). Gene transfer to plants: Assessment of published approaches and results. Annual Review of Plant Physiology and Plant Molecular Biology, vol. 42, p. 205-225.
Punt, P. et. al. (2002). Filamentous fungi as cell factories for heterologous protein production. Trends in Biotechnology, vol. 20, No. 5, p. 200-206.
Riccio, M.L. et. al. (1997). Expression cloning of different bacterial phosphatase-encoding genes by histochemical screening of genomic libraries onto an indicator medium containing phenolphthalein diphosphate and methyl green. Journal of Applied Microbiology, vol. 82, p. 177-185.
Saiki, R. et. al. (1988). Primer-Directed Enzymatic Amplification of DNA with a thermostable DNA polymerase. Science, v. 239, p. 487-491.
Sandberg, A. et. al. (1986). HPLC Method for determination of Inositol Tri-, Tetra-, Penta-, and Hexaphosphates in foods and intestinal contents. Journal of Food and Science, vol. 51, No. 3, p. 547-550.
Simon, R. et. al., (1992). Peptoids: A modular approach to drug discovery. Proc. Natl Acad Sci., vol. 89, No. 20, p. 9367-9371.
Takeda, S. et. al. (1985). Construction of chimaeric processed immunoglobulin genes containing mouse variable and human constant region sequence. Nature, vol. 314, p. 452-454.

Tatusova, T. et. al. (1999). A new tool for comparing protein and nucleotide sequences. FEMS Microbiology Letters, vol. 174, No. 2, p. 247-250.

Tatusova, T. et. al. (1999). Erratum to BLAST 2 Sequences, a new tool for comparing protein and nucleotide sequence. FEMS Microbiology Letters, vol. 177, No. 1, p. 187-188.

Trueman, L. (1995). Heterologous Expression in Yeast. Molecular Biology, vol. 49, chap. 27, p. 341-354.

Turner, G. (1994). Vectors for genetic manipulation. Progress in Industrial Microbiology, vol. 29, chap. 24, p. 641-666.

Wodzinski, R. et. al. (1996). Phytase. Advances in Applied Microbiology, vol. 42, p. 263-302.

Abstract: Deluca, et al., Identification of Phytase from *Citrobacter freundii*, General Meeting of the American Society for Microbiology (1992) vol. 92, p. 385 Q-302.

* cited by examiner

SEQUENCE LISTING

```
<160> NUMBER OF SEQ ID NOS: 8

<210> SEQ ID NO 1
<211> LENGTH: 823
<212> TYPE: DNA
<213> ORGANISM: Citrobacter freundii

<400> SEQUENCE: 1
cgattactag cgattccgac ttctggagtc gagttgcaga ctccaatccg gactacgaca      60
tactttatga ggtccgcttg ctctcgcgag gtcgcttctc tttgtatatg ccattgtagc     120
acgtgtgtag ccctactcgt aagggccatg atgacttgac gtcatcccca ccttcctcca     180
gtttatcact ggcagtctcc tttgagttcc cggccgaacc gctggcaaca aaggataagg     240
gttgcgctcg ttgcgggact taacccaaca tttcacaaca cgagctgacg acagccatgc     300
agcacctgtc tcagagttcc cgaaggcacc aaagcatctc tgctaagttc tctggatgtc     360
aagagtaggt aaggttcttc gcgttgcatc gaattaaacc acatgctcca ccgcttgtgc     420
gggcccccgt caattcattt gagttttaac cttgcggccg tactccccag gcggtcgact     480
taacgcgtta gctccggaag ccacgcctca agggcacaac ctccaagtcg acatcgttta     540
cggcgtggac taccagggta tctaatcctg tttgctcccc acgctttcgc acctgagcgt     600
cagtctttgt ccagggggcc gccttcgcca ccggtattcc tccagatctc tacgcatttc     660
accgctacac ctggaattct accccctct acaagactct agcctgccag tttcggatgc     720
agttcccagg ttgagcccgg ggatttcaca tccgacttga cagaccgcct gcgtgcgctt     780
tacgcccagt aattccgatt aacgcttgca ccctccgtat tac                       823

<210> SEQ ID NO 2
<211> LENGTH: 1401
<212> TYPE: DNA
<213> ORGANISM: Citrobacter freundii

<400> SEQUENCE: 2
aaaggtggtg ctggtaatga gtacattcat cattcgttta ttatttttt ctctcttatg      60
```

```
cggttctttc tcaatacatg ctgaagagcc gaacggtatg aaacttgagc gggttgtgat    120
agtgagccgt catggagtaa gagcacctac gaagttcact ccaataatga aagatgttac    180
acccgatcaa tggccacaat gggatgtgcc gttaggatgg ctaacgcctc gtggggagaa    240
acttgtttct gaattaggtc agtatcaacg tttatggttc acaagcaaag gtctgttgaa    300
taatcaaacg tgcccatctc cagggcaggt tgctgttatt gcagacacgg atcaacgcac    360
ccgtaaaacg ggtgaggcgt tcctggctgg gttagcacca aaatgtcaaa ttcaagtgca    420
ttatcagaag gatgaagaaa aaactgatcc tcttttaat ccagtaaaaa tggggacatg     480
ttcgtttaac acattgaagg ttaaaaacgc tattctggaa cgggccggag gaaatattga    540
actgtatacc caacgctatc aatcttcatt tcggaccctg aaaatgtttt aaatttctc    600
acaatcggag acatgtaaga ctacagaaaa gtctacgaaa tgcacattac cagaggcttt    660
accgtctgaa cttaaggtaa ctcctgacaa tgtatcatta cctggtgcct ggagtctttc    720
ttccacgctg actgagatat ttctgttgca agaggcccag ggaatgccac aggtagcctg    780
ggggcgtatt acgggagaaa aagaatggag agatttgtta agtctgcata acgctcagtt    840
tgatcttttg caaagaactc cagaagttgc ccgtagtagg gccacaccat tactcgatat    900
gatagacact gcattattga caaatggtac aacagaaaac aggtatggca taaaattacc    960
cgtatctctg ttgtttattg ctggtcatga taccaatctt gcaaatttaa gcggggcttt   1020
agatcttaac tggtcgctgc ccggtcaacc cgataatacc cctcctggtg gggagcttgt   1080
attcgaaaag tggaaaagaa ccagtgataa tacggattgg gttcaggttt catttgttta   1140
tcagacgctg agagatatga gggatataca accgttgtcg ttagaaaaac ctgccggcaa   1200
agttgattta aaattaattg catgtgaaga gaaaaatagt cagggaatgt gttcgttaaa   1260
aagttttcc aggctcatta aggaaattcg cgtgccagag tgtgcagtta cggaataagt    1320
aactaattac tatatatagc gtattaaaaa atagaaaccc ccggtttgta gtcgggggta   1380
ttcgtattgt tcataattac a                                              1401
```

<210> SEQ ID NO 3
<211> LENGTH: 433
<212> TYPE: PRT
<213> ORGANISM: Citrobacter freundii

<400> SEQUENCE: 3

```
Met Ser Thr Phe Ile Ile Arg Leu Leu Phe Phe Ser Leu Leu Cys Gly
1               5                   10                  15

Ser Phe Ser Ile His Ala Glu Glu Pro Asn Gly Met Lys Leu Glu Arg
            20                  25                  30

Val Val Ile Val Ser Arg His Gly Val Arg Ala Pro Thr Lys Phe Thr
        35                  40                  45

Pro Ile Met Lys Asp Val Thr Pro Asp Gln Trp Pro Gln Trp Asp Val
    50                  55                  60

Pro Leu Gly Trp Leu Thr Pro Arg Gly Gly Glu Leu Val Ser Glu Leu
65                  70                  75                  80

Gly Gln Tyr Gln Arg Leu Trp Phe Thr Ser Lys Gly Leu Leu Asn Asn
                85                  90                  95

Gln Thr Cys Pro Ser Pro Gly Gln Val Ala Val Ile Ala Asp Thr Asp
            100                 105                 110

Gln Arg Thr Arg Lys Thr Gly Glu Ala Phe Leu Ala Gly Leu Ala Pro
        115                 120                 125

Lys Cys Gln Ile Gln Val His Tyr Gln Lys Asp Glu Glu Lys Thr Asp
```

```
                130             135             140
Pro Leu Phe Asn Pro Val Lys Met Gly Thr Cys Ser Phe Asn Thr Leu
145                 150                 155                 160

Lys Val Lys Asn Ala Ile Leu Glu Arg Ala Gly Gly Asn Ile Glu Leu
                165                 170                 175

Tyr Thr Gln Arg Tyr Gln Ser Ser Phe Arg Thr Leu Glu Asn Val Leu
                180                 185                 190

Asn Phe Ser Gln Ser Glu Thr Cys Lys Thr Thr Glu Lys Ser Thr Lys
                195                 200                 205

Cys Thr Leu Pro Glu Ala Leu Pro Ser Glu Leu Lys Val Thr Pro Asp
210                 215                 220

Asn Val Ser Leu Pro Gly Ala Trp Ser Leu Ser Ser Thr Leu Thr Glu
225                 230                 235                 240

Ile Phe Leu Leu Gln Glu Ala Gln Gly Met Pro Gln Val Ala Trp Gly
                245                 250                 255

Arg Ile Thr Gly Glu Lys Glu Trp Arg Asp Leu Leu Ser Leu His Asn
                260                 265                 270

Ala Gln Phe Asp Leu Leu Gln Arg Thr Pro Glu Val Ala Arg Ser Arg
                275                 280                 285

Ala Thr Pro Leu Leu Asp Met Ile Asp Thr Ala Leu Leu Thr Asn Gly
290                 295                 300

Thr Thr Glu Asn Arg Tyr Gly Ile Lys Leu Pro Val Ser Leu Leu Phe
305                 310                 315                 320

Ile Ala Gly His Asp Thr Asn Leu Ala Asn Leu Ser Gly Ala Leu Asp
                325                 330                 335

Leu Asn Trp Ser Leu Pro Gly Gln Pro Asp Asn Thr Pro Pro Gly Gly
                340                 345                 350

Glu Leu Val Phe Glu Lys Trp Lys Arg Thr Ser Asp Asn Thr Asp Trp
                355                 360                 365

Val Gln Val Ser Phe Val Tyr Gln Thr Leu Arg Asp Met Arg Asp Ile
                370                 375                 380

Gln Pro Leu Ser Leu Glu Lys Pro Ala Gly Lys Val Asp Leu Lys Leu
385                 390                 395                 400

Ile Ala Cys Glu Glu Lys Asn Ser Gln Gly Met Cys Ser Leu Lys Ser
                405                 410                 415

Phe Ser Arg Leu Ile Lys Glu Ile Arg Val Pro Glu Cys Ala Val Thr
                420                 425                 430

Glu

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide primer 536f

<400> SEQUENCE: 4
cagcmgccgc ggtaatwc                                                 18

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide primer 1392r

<400> SEQUENCE: 5
```

-continued acgggcggtg tgtrc                                                15

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide primer o42-5

<400> SEQUENCE: 6
ggaattcata tgagtacatt catcattcg                                 29

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide primer o42-3

<400> SEQUENCE: 7
ggaattcgga tcccttattc cgtaactgca cac                            33

<210> SEQ ID NO 8
<211> LENGTH: 433
<212> TYPE: PRT
<213> ORGANISM: Citrobacter freundii
<220> FEATURE:
<221> NAME/KEY: SITE
<222> LOCATION: (22)..(22)
<223> OTHER INFORMATION: Xaa may be Ala or Thr
<220> FEATURE:
<221> NAME/KEY: SITE
<222> LOCATION: (23)..(23)
<223> OTHER INFORMATION: Xaa may be Glu, Lys or Gln
<220> FEATURE:
<221> NAME/KEY: SITE
<222> LOCATION: (24)..(24)
<223> OTHER INFORMATION: Xaa may be Glu or Asp
<220> FEATURE:
<221> NAME/KEY: SITE
<222> LOCATION: (28)..(28)
<223> OTHER INFORMATION: Xaa may be Met or Leu
<220> FEATURE:
<221> NAME/KEY: SITE
<222> LOCATION: (46)..(46)
<223> OTHER INFORMATION: Xaa may be Lys, Glu or Arg
<220> FEATURE:
<221> NAME/KEY: SITE
<222> LOCATION: (53)..(53)
<223> OTHER INFORMATION: Xaa may be Asp, Lys or Asn
<220> FEATURE:
<221> NAME/KEY: SITE
<222> LOCATION: (57)..(57)
<223> OTHER INFORMATION: Xaa may be Asp or Tyr
<220> FEATURE:
<221> NAME/KEY: SITE
<222> LOCATION: (67)..(67)
<223> OTHER INFORMATION: Xaa may be Gly or Arg
<220> FEATURE:
<221> NAME/KEY: SITE
<222> LOCATION: (74)..(74)
<223> OTHER INFORMATION: Xaa may be Gly or Arg
<220> FEATURE:
<221> NAME/KEY: SITE
<222> LOCATION: (75)..(75)
<223> OTHER INFORMATION: Xaa may be Glu, Lys or Val
<220> FEATURE:
<221> NAME/KEY: SITE
<222> LOCATION: (77)..(77)
<223> OTHER INFORMATION: Xaa may be Val or Ile
<220> FEATURE:
<221> NAME/KEY: SITE
<222> LOCATION: (78)..(78)
<223> OTHER INFORMATION: Xaa may be Ser or Thr
<220> FEATURE:

-continued

```
<221> NAME/KEY: SITE
<222> LOCATION: (79)..(79)
<223> OTHER INFORMATION: Xaa may be Glu or Val
<220> FEATURE:
<221> NAME/KEY: SITE
<222> LOCATION: (82)..(82)
<223> OTHER INFORMATION: Xaa may be Gln, His, Lys or Arg
<220> FEATURE:
<221> NAME/KEY: SITE
<222> LOCATION: (88)..(88)
<223> OTHER INFORMATION: Xaa may be Phe or Tyr
<220> FEATURE:
<221> NAME/KEY: SITE
<222> LOCATION: (95)..(95)
<223> OTHER INFORMATION: Xaa may be Asn, Asp or Pro
<220> FEATURE:
<221> NAME/KEY: SITE
<222> LOCATION: (96)..(96)
<223> OTHER INFORMATION: Xaa may be Asn, Pro, Ser or Tyr
<220> FEATURE:
<221> NAME/KEY: SITE
<222> LOCATION: (97)..(97)
<223> OTHER INFORMATION: Xaa may be Gln or Thr
<220> FEATURE:
<221> NAME/KEY: SITE
<222> LOCATION: (98)..(98)
<223> OTHER INFORMATION: Xaa may be Thr, Gly or Pro
<220> FEATURE:
<221> NAME/KEY: SITE
<222> LOCATION: (101)..(101)
<223> OTHER INFORMATION: Xaa may be Ser or Phe
<220> FEATURE:
<221> NAME/KEY: SITE
<222> LOCATION: (102)..(102)
<223> OTHER INFORMATION: Xaa may be Pro or Leu
<220> FEATURE:
<221> NAME/KEY: SITE
<222> LOCATION: (103)..(103)
<223> OTHER INFORMATION: Xaa may be Gly or Glu
<220> FEATURE:
<221> NAME/KEY: SITE
<222> LOCATION: (105)..(105)
<223> OTHER INFORMATION: Xaa may be Val or Ile
<220> FEATURE:
<221> NAME/KEY: SITE
<222> LOCATION: (109)..(109)
<223> OTHER INFORMATION: Xaa may be Ala or Thr
<220> FEATURE:
<221> NAME/KEY: SITE
<222> LOCATION: (112)..(112)
<223> OTHER INFORMATION: Xaa may be Asp, Val or Tyr
<220> FEATURE:
<221> NAME/KEY: SITE
<222> LOCATION: (122)..(122)
<223> OTHER INFORMATION: Xaa may be Phe or Tyr
<220> FEATURE:
<221> NAME/KEY: SITE
<222> LOCATION: (126)..(126)
<223> OTHER INFORMATION: Xaa may be Leu or Ile
<220> FEATURE:
<221> NAME/KEY: SITE
<222> LOCATION: (136)..(136)
<223> OTHER INFORMATION: Xaa may be Tyr or Asn
<220> FEATURE:
<221> NAME/KEY: SITE
<222> LOCATION: (140)..(140)
<223> OTHER INFORMATION: Xaa may be Glu or Val
<220> FEATURE:
<221> NAME/KEY: SITE
<222> LOCATION: (142)..(142)
<223> OTHER INFORMATION: Xaa may be Lys or Arg
<220> FEATURE:
<221> NAME/KEY: SITE
<222> LOCATION: (143)..(143)
<223> OTHER INFORMATION: Xaa may be Thr, Ile or Pro
<220> FEATURE:
<221> NAME/KEY: SITE
<222> LOCATION: (148)..(148)
<223> OTHER INFORMATION: Xaa may be Asn or Asp
<220> FEATURE:
```

```
<221> NAME/KEY: SITE
<222> LOCATION: (151)..(151)
<223> OTHER INFORMATION: Xaa may be Lys or Gly
<220> FEATURE:
<221> NAME/KEY: SITE
<222> LOCATION: (152)..(152)
<223> OTHER INFORMATION: Xaa may be Met, Lys or Val
<220> FEATURE:
<221> NAME/KEY: SITE
<222> LOCATION: (154)..(154)
<223> OTHER INFORMATION: Xaa may be Thr or Ile
<220> FEATURE:
<221> NAME/KEY: SITE
<222> LOCATION: (156)..(156)
<223> OTHER INFORMATION: Xaa may be Ser or Thr
<220> FEATURE:
<221> NAME/KEY: SITE
<222> LOCATION: (160)..(160)
<223> OTHER INFORMATION: Xaa may be Leu or Phe
<220> FEATURE:
<221> NAME/KEY: SITE
<222> LOCATION: (161)..(161)
<223> OTHER INFORMATION: Xaa may be Lys or Asn
<220> FEATURE:
<221> NAME/KEY: SITE
<222> LOCATION: (164)..(164)
<223> OTHER INFORMATION: Xaa may be Asn or Asp
<220> FEATURE:
<221> NAME/KEY: SITE
<222> LOCATION: (168)..(168)
<223> OTHER INFORMATION: Xaa may be Glu or Asp
<220> FEATURE:
<221> NAME/KEY: SITE
<222> LOCATION: (170)..(170)
<223> OTHER INFORMATION: Xaa may be Ala or Thr
<220> FEATURE:
<221> NAME/KEY: SITE
<222> LOCATION: (176)..(176)
<223> OTHER INFORMATION: Xaa may be Leu, Gln or Val
<220> FEATURE:
<221> NAME/KEY: SITE
<222> LOCATION: (177)..(177)
<223> OTHER INFORMATION: Xaa may be Tyr or Phe
<220> FEATURE:
<221> NAME/KEY: SITE
<222> LOCATION: (195)..(195)
<223> OTHER INFORMATION: Xaa may be Ser or Thr
<220> FEATURE:
<221> NAME/KEY: SITE
<222> LOCATION: (199)..(199)
<223> OTHER INFORMATION: Xaa may be Thr or Ile
<220> FEATURE:
<221> NAME/KEY: SITE
<222> LOCATION: (203)..(203)
<223> OTHER INFORMATION: Xaa may be Thr, Ile, Leu, Ser or Trp
<220> FEATURE:
<221> NAME/KEY: SITE
<222> LOCATION: (204)..(204)
<223> OTHER INFORMATION: Xaa may be Glu, Ala, Gly, His, Ile, Asn, Arg or
      Val
<220> FEATURE:
<221> NAME/KEY: SITE
<222> LOCATION: (205)..(205)
<223> OTHER INFORMATION: Xaa may be Lys, Pro or Arg
<220> FEATURE:
<221> NAME/KEY: SITE
<222> LOCATION: (206)..(206)
<223> OTHER INFORMATION: Xaa may be Ser, Arg or Thr
<220> FEATURE:
<221> NAME/KEY: SITE
<222> LOCATION: (207)..(207)
<223> OTHER INFORMATION: Xaa may be Thr, Ala or Ser
<220> FEATURE:
<221> NAME/KEY: SITE
<222> LOCATION: (215)..(215)
<223> OTHER INFORMATION: Xaa may be Leu or Phe
<220> FEATURE:
<221> NAME/KEY: SITE
<222> LOCATION: (224)..(224)
<223> OTHER INFORMATION: Xaa may be Asp or His
```

```
<220> FEATURE:
<221> NAME/KEY: SITE
<222> LOCATION: (225)..(225)
<223> OTHER INFORMATION: Xaa may be Asn, Asp or Glu
<220> FEATURE:
<221> NAME/KEY: SITE
<222> LOCATION: (229)..(229)
<223> OTHER INFORMATION: Xaa may be Pro or Ser
<220> FEATURE:
<221> NAME/KEY: SITE
<222> LOCATION: (233)..(233)
<223> OTHER INFORMATION: Xaa may be Ser or Cys
<220> FEATURE:
<221> NAME/KEY: SITE
<222> LOCATION: (235)..(235)
<223> OTHER INFORMATION: Xaa may be Ser or Ala
<220> FEATURE:
<221> NAME/KEY: SITE
<222> LOCATION: (274)..(274)
<223> OTHER INFORMATION: Xaa may be Gln, His or Leu
<220> FEATURE:
<221> NAME/KEY: SITE
<222> LOCATION: (279)..(279)
<223> OTHER INFORMATION: Xaa may be Gln or Glu
<220> FEATURE:
<221> NAME/KEY: SITE
<222> LOCATION: (288)..(288)
<223> OTHER INFORMATION: Xaa may be Arg or Met
<220> FEATURE:
<221> NAME/KEY: SITE
<222> LOCATION: (301)..(301)
<223> OTHER INFORMATION: Xaa may be Leu or Ser
<220> FEATURE:
<221> NAME/KEY: SITE
<222> LOCATION: (307)..(307)
<223> OTHER INFORMATION: Xaa may be Glu or Tyr
<220> FEATURE:
<221> NAME/KEY: SITE
<222> LOCATION: (308)..(308)
<223> OTHER INFORMATION: Xaa may be Asn, Asp or Thr
<220> FEATURE:
<221> NAME/KEY: SITE
<222> LOCATION: (322)..(322)
<223> OTHER INFORMATION: Xaa may be Ala or Val
<220> FEATURE:
<221> NAME/KEY: SITE
<222> LOCATION: (343)..(343)
<223> OTHER INFORMATION: Xaa may be Gly or Ala
<220> FEATURE:
<221> NAME/KEY: SITE
<222> LOCATION: (358)..(358)
<223> OTHER INFORMATION: Xaa may be Lys or Arg
<220> FEATURE:
<221> NAME/KEY: SITE
<222> LOCATION: (360)..(360)
<223> OTHER INFORMATION: Xaa may be Lys or Asn
<220> FEATURE:
<221> NAME/KEY: SITE
<222> LOCATION: (362)..(362)
<223> OTHER INFORMATION: Xaa may be Thr, Ala or Ile
<220> FEATURE:
<221> NAME/KEY: SITE
<222> LOCATION: (365)..(365)
<223> OTHER INFORMATION: Xaa may be Asn or Asp
<220> FEATURE:
<221> NAME/KEY: SITE
<222> LOCATION: (366)..(366)
<223> OTHER INFORMATION: Xaa may be Thr or Ser
<220> FEATURE:
<221> NAME/KEY: SITE
<222> LOCATION: (367)..(367)
<223> OTHER INFORMATION: Xaa may be Asp or Asn
<220> FEATURE:
<221> NAME/KEY: SITE
<222> LOCATION: (370)..(370)
<223> OTHER INFORMATION: Xaa may be Gln or His
<220> FEATURE:
<221> NAME/KEY: SITE
<222> LOCATION: (383)..(383)
<223> OTHER INFORMATION: Xaa may be Asp or Val
```

```
<220> FEATURE:
<221> NAME/KEY: SITE
<222> LOCATION: (384)..(384)
<223> OTHER INFORMATION: Xaa may be Ile, Phe, Leu or Met
<220> FEATURE:
<221> NAME/KEY: SITE
<222> LOCATION: (385)..(385)
<223> OTHER INFORMATION: Xaa may be Gln or Arg
<220> FEATURE:
<221> NAME/KEY: SITE
<222> LOCATION: (386)..(386)
<223> OTHER INFORMATION: Xaa may be Pro or Gln
<220> FEATURE:
<221> NAME/KEY: SITE
<222> LOCATION: (391)..(391)
<223> OTHER INFORMATION: Xaa may be Lys or Asn
<220> FEATURE:
<221> NAME/KEY: SITE
<222> LOCATION: (393)..(393)
<223> OTHER INFORMATION: Xaa may be Ala or Pro
<220> FEATURE:
<221> NAME/KEY: SITE
<222> LOCATION: (395)..(395)
<223> OTHER INFORMATION: Xaa may be Lys or Thr
<220> FEATURE:
<221> NAME/KEY: SITE
<222> LOCATION: (397)..(397)
<223> OTHER INFORMATION: Xaa may be Asp or Asn
<220> FEATURE:
<221> NAME/KEY: SITE
<222> LOCATION: (408)..(408)
<223> OTHER INFORMATION: Xaa may be Ser or Ile
<220> FEATURE:
<221> NAME/KEY: SITE
<222> LOCATION: (414)..(414)
<223> OTHER INFORMATION: Xaa may be Leu or Ile

<400> SEQUENCE: 8

Met Ser Thr Phe Ile Ile Arg Leu Leu Phe Phe Ser Leu Leu Cys Gly
 1               5                  10                  15

Ser Phe Ser Ile His Xaa Xaa Xaa Pro Asn Gly Xaa Lys Leu Glu Arg
                20                  25                  30

Val Val Ile Val Ser Arg His Gly Val Arg Ala Pro Thr Xaa Phe Thr
            35                  40                  45

Pro Ile Met Lys Xaa Val Thr Pro Xaa Gln Trp Pro Gln Trp Asp Val
 50                  55                  60

Pro Leu Xaa Trp Leu Thr Pro Arg Gly Xaa Xaa Leu Xaa Xaa Xaa Leu
65                  70                  75                  80

Gly Xaa Tyr Gln Arg Leu Trp Xaa Thr Ser Lys Gly Leu Leu Xaa Xaa
                85                  90                  95

Xaa Xaa Cys Pro Xaa Xaa Xaa Gln Xaa Ala Val Ile Xaa Asp Thr Xaa
            100                 105                 110

Gln Arg Thr Arg Lys Thr Gly Glu Ala Xaa Leu Ala Gly Xaa Ala Pro
            115                 120                 125

Lys Cys Gln Ile Gln Val His Xaa Gln Lys Asp Xaa Glu Xaa Xaa Asp
130                 135                 140

Pro Leu Phe Xaa Pro Val Xaa Xaa Gly Xaa Cys Xaa Phe Asn Thr Xaa
145                 150                 155                 160

Xaa Val Lys Xaa Ala Ile Leu Xaa Arg Xaa Gly Gly Asn Ile Glu Xaa
                165                 170                 175

Xaa Thr Gln Arg Tyr Gln Ser Ser Phe Arg Thr Leu Glu Asn Val Leu
            180                 185                 190

Asn Phe Xaa Gln Ser Glu Xaa Cys Lys Thr Xaa Xaa Xaa Xaa Xaa Lys
            195                 200                 205

Cys Thr Leu Pro Glu Ala Xaa Pro Ser Glu Leu Lys Val Thr Pro Xaa
210                 215                 220
```

-continued

```
Xaa Val Ser Leu Xaa Gly Ala Trp Xaa Leu Xaa Ser Thr Leu Thr Glu
225             230             235             240

Ile Phe Leu Leu Gln Glu Ala Gln Gly Met Pro Gln Val Ala Trp Gly
                245             250             255

Arg Ile Thr Gly Glu Lys Glu Trp Arg Asp Leu Leu Ser Leu His Asn
            260             265             270

Ala Xaa Phe Asp Leu Leu Xaa Arg Thr Pro Glu Val Ala Arg Ser Xaa
        275             280             285

Ala Thr Pro Leu Leu Asp Met Ile Asp Thr Ala Leu Xaa Thr Asn Gly
    290             295             300

Thr Thr Xaa Xaa Arg Tyr Gly Ile Lys Leu Pro Val Ser Leu Leu Phe
305             310             315             320

Ile Xaa Gly His Asp Thr Asn Leu Ala Asn Leu Ser Gly Ala Leu Asp
            325             330             335

Leu Asn Trp Ser Leu Pro Xaa Gln Pro Asp Asn Thr Pro Pro Gly Gly
            340             345             350

Glu Leu Val Phe Glu Xaa Trp Xaa Arg Xaa Ser Asp Xaa Xaa Xaa Trp
            355             360             365

Val Xaa Val Ser Phe Val Tyr Gln Thr Leu Arg Asp Met Arg Xaa Xaa
    370             375             380

Xaa Xaa Leu Ser Leu Glu Xaa Pro Xaa Gly Xaa Val Xaa Leu Lys Leu
385             390             395             400

Ile Ala Cys Glu Glu Lys Asn Xaa Gln Gly Met Cys Ser Xaa Lys Ser
                405             410             415

Phe Ser Arg Leu Ile Lys Glu Ile Arg Val Pro Glu Cys Ala Val Thr
            420             425             430

Glu
```

MUTANT *CITROBACTER FREUNDII* PHYTASE POLYPEPTIDE

REFERENCE TO RELATED APPLICATIONS

This application is a continuation-in-part of International Patent Application PCT/IB2005/003660 filed Oct. 4, 2005 which published as WO 2006/038128 on Apr. 13, 2006, and which claims priority to International Patent Application PCT/IB2005/000598 filed Feb. 15, 2005, and Great Britain Patent Application No. 0422052.1 filed Oct. 4, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

The present invention relates to phytases, nucleotide sequences for same, methods of production of phytases and their use.

FIELD OF THE INVENTION

The present invention relates to the field of enzymes for additives to feedstuffs. More specifically, the present invention relates to phytases which can be used for enhancing phosphate digestion in foods and animal feeds.

TECHNICAL BACKGROUND AND PRIOR ART

Phytate is the major storage form of phosphorus in cereals and legumes. However, monogastric animals such as pig, poultry and fish are not able to metabolise or absorb phytate (or phytic acid) and therefore it is excreted leading to phosphorous pollution in areas of intense livestock production. Moreover phytic acid also acts as an antinutritional agent in monogastric animals by chelating metal agents such as calcium, copper and zinc.

In order to provide sufficient phosphates for growth and health of these animals, inorganic phosphate is added to their diets. Such addition can be costly and further increases pollution problems.

Phytate is converted by phytases which generally catalyse the hydrolysis of phytate to lower inositol-phosphates and inorganic phosphate. Phytases are useful as additives to animal feeds where they improve the availability of organic phosphorus to the animal and decrease phosphate pollution of the environment (Wodzinski R J, Ullah A H. Adv Appl Microbiol. 42, 263-302 (1996)).

A number of phytases of fungal (Wyss M. et al. Appl. Environ. Microbiol. 65 (2), 367-373 (1999); Berka R. M. et al. Appl. Environ. Microbiol. 64 (11), 4423-4427 (1998); Lassen S. et al. Appl. Environ. Microbiol. 67 (10), 4701-4707 (2001)) and bacterial (Greiner R. et al Arch. Biochem. Biophys. 303 (1), 107-113 (1993); Kerovuo et al. Appl. Environ. Microbiol. 64 (6), 2079-2085 (1998); Kim H. W. et al. Biotechnol. Lett. 25, 1231-1234 (2003); Greiner R. et al. Arch. Biochem. Biophys. 341 (2), 201-206 (1997); Yoon S. J. et al. Enzyme and microbial technol. 18, 449-454 (1996); Zinin N. V. et al. FEMS Microbiol. Lett. 236, 283-290 (2004))) origin have been described in the literature.

However, to date, none of these phytases display the properties required for effective use as an animal feed supplement. In particular, fungal phytases tend to be proteolytically unstable (Igbasan F. A. et al. Arch. Anim. Nutr. 53, 353-373 (2000)) and therefore susceptible to degradation, while most bacterial phytases have a narrow substrate specificity for phytate alone and degrade poorly inositol phosphates of intermediate degrees of phosphorylation (Greiner R. et al., Arch. Biochem. Biophys. 303 (1), 107-113 (1993); Kerovuo J et al. Biochem. J. 352, 623-628 (2000)).

Accordingly, there is a need for improved phytases.

SUMMARY OF THE INVENTION

In a broad aspect, the present invention relates to phytases derived from a bacterium and modified forms thereof. In particular the invention relates to wild type phytases derived from the bacterium, *Citrobacter freundii*, and variant/modified forms thereof showing improved characteristics compared to the wild-type enzyme.

The present invention is advantageous as it provides for novel phytases that have properties making them particularly useful and efficient as feed enzymes. In particular the invention relates to isolated and/or purified novel phytase polypeptide as described herein or functional fragments or variants or modified forms thereof. The invention also provides the nucleic acid and amino acid sequences encoding said phytases.

To be efficient as an enzyme additive to food or animal feed, a phytase has to combine a number of different properties. In order to be able to degrade phytic acid in the acidic environment of an animal's stomach it has to be active at low pH, preferably over a broad range of pH values. In addition, it has to have high specific activity and preferably high thermostability to enable the protein to withstand high temperatures commonly used in preparation of feedstuffs such as feed pellets.

It is also important that the enzyme has broad substrate specificity allowing it to hydrolyse not only phytate but also intermediate products of phytate degradation such as inositol pentaphosphates, tetraphosphates and triphosphates. Studies on phytate degradation in pigs show that these inositol oligophosphates otherwise remain largely insoluble in the small and large intestine and thus inaccessible to alkaline phosphatases produced by the animal and gut microflora (Schlemmer U. et al. Arch. Anim. Nutr. 55, 255-280 (2001)). Variations in substrate specificity profiles of different enzymes have been identified. For example, inositol-triphosphates generated by the phytase from *B. subtilis* are essentially resistant to further hydrolysis by this enzyme (Kerovuo J. et al. Biochem J. (200) 352, 623-628).

In another aspect of the invention there is provided a plasmid or a vector system or a transformed or a transgenic organism comprising a novel phytase as described herein or a modified form thereof.

In another aspect the present invention relates to transgenic organisms modified to express a novel phytase as described herein or a modified form thereof and therefore being capable of producing a phytase. The present invention further provides means and methods for the biotechnological production of phytases and their use as feed supplements.

Aspects of the present invention are presented in the claims and in the following commentary.

For ease of reference, these and further aspects of the present invention are now discussed under appropriate section headings. However, the teachings under each section are not necessarily limited to each particular section.

As used with reference to the present invention, the terms "produce", "producing", "produced", "producible", "production" are synonymous with the respective terms "prepare", "preparing", "prepared", "preparation", "generated", "generation" and "preparable".

As used with reference to the present invention, the terms "expression", "expresses", "expressed" and "expressable" are synonymous with the respective terms "transcription", "transcribes", "transcribed" and "transcribable".

As used with reference to the present invention, the terms "transformation" and "transfection" refer to a method of introducing nucleic acid sequences into hosts, host cells, tissues or organs.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same. The present invention further encompasses methods of isolating the nucleotide sequence, such as isolating from a host cell.

Other aspects concerning the amino acid sequences for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequences for use in the present invention using the same, such as expression in a host cell; including methods of transferring same, and then purifying said sequence.

Figure 1:
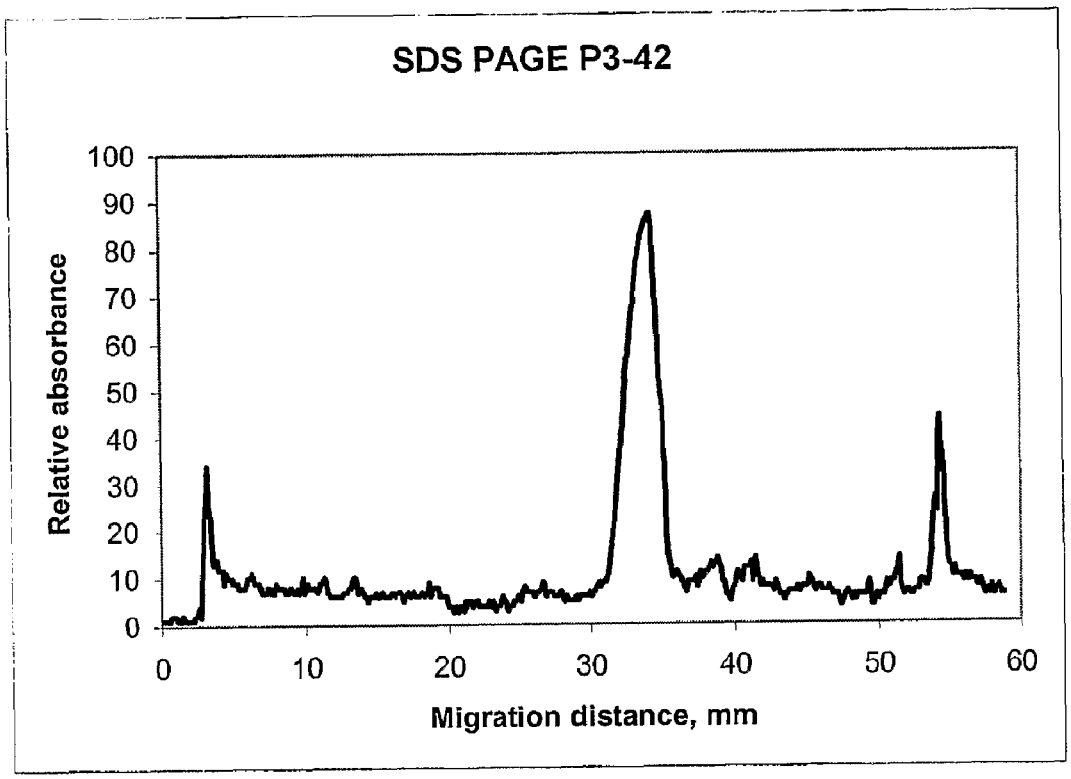
FIG. 1 shows SDS PAGE analysis of the recombinant phytase from *C. freundii* P3-42 purified by DEAE-Sepharose chromatography. The figure presents the scanning trace of a digital photographic image of the lane containing a sample of the *C. freundii* phytase.

SEQ ID NO: 1 lists the sequence obtained for identification of the bacterial strain.

SEQ ID NO: 2 lists the sequence comprising the phytase gene from *C. freundii* P3-42.

SEQ ID NO: 3 lists the amino acid sequence of the phytase gene *C. freundii* P3-42.

SEQ ID NO:8 lists the amino acid sequence of the phytase gene *C. freundii* P3-42 with possible amino acid substitutions marked.

DETAILED DISCLOSURE OF INVENTION

The present invention features an enzyme comprising the amino acid sequence corresponding to *Citrobacter freundii* phytase or a modified form, a variant, a functional equivalent or an effective fragment thereof.

The term "phytase" means a protein or polypeptide which is capable of catalysing the hydrolysis of esters of phosphoric acid including phytate and releasing inorganic phosphate. Phytases are capable to hydrolyse, in addition to phytate, at least some of the inositol-phosphates of intermediate degrees of phosphorylation.

The term "corresponding to *Citrobacter freundii* phytase" means that the enzyme need not have been obtained from a source of *Citrobacter freundii*. Instead, the enzyme has to have essentially the same functional characteristics or sequence as that of *Citrobacter freundii* phytase.

The term "functional equivalent thereof" means that the enzyme has to have essentially the same functional characteristics as that of wild-type *Citrobacter freundii* phytase. The term "modified form" or "variant" means that the enzyme has been modified from its original form but retains essentially the same enzymatic functional characteristics as that of wild-type *Citrobacter freundii* phytase. In particular, the terms "variant" or "modified form" encompass phytase enzymes with an amino acid sequence derived from the amino acid sequence of the parent/wild-type phytase and having one or more amino acid substitutions, insertions, and/or deletions, which together are referred to as mutations. Modified forms or variants may be altered in the enzyme characteristics compared to the parent enzyme. Preferably, modified forms or variants have an increased thermostability, an increased pepsin stability, an increased specific activity, a broader substrate specificity, or other modifications that are beneficial for the application of the enzyme. The term "functional" or "effective" fragment means a fragment or portion of the *Citrobacter freundii* phytase that retains essentially the same enzymatic function or effect.

Preferably the enzyme of this aspect of the present invention has the same sequence or a sequence that is at least 75% identical (homologous) to that of *Citrobacter freundii* phytase.

Suitably, the enzyme comprises the amino acid sequence as shown in SEQ ID NO: 3 or a sequence having at least 75% identity (homology) thereto or a functional fragment thereof. In a preferred embodiment, the invention provides an isolated and/or purified polypeptide having the amino acid sequence as set out in SEQ ID NO: 3 or a sequence having at least 75% identity (homology) thereto or an effective fragment thereof. In another embodiment, the phytase is characterised in that it is derived from *Citrobacter freundii* strain P3-42 deposited under accession number NCMB 41247 on Sep. 22, 2004, under the terms of the Budapest Treaty, with the National Collections of Industrial, Marine and Food Bacteria (NCIMB) in Bucksburn, Aberdeen AB21 9YA, Scotland, UK. Deposited microorganism(s) will be irrevocably and without restriction or condition released to the public during the effective term of any patent issued from this application.

In a preferred embodiment, the invention relates to a phytase in accordance with any embodiment of the first aspect of the invention that comprises one or more mutations at the following positions (numbering according to the numbering in SEQ ID No. 3): 22, 23, 24, 28, 46, 53, 57, 67, 74, 75, 77, 78, 79, 82, 88, 95, 96, 97, 98, 101, 102, 103, 105, 109, 112, 122, 126, 136, 140, 142, 143, 148, 151, 152, 154, 156, 160, 161, 164, 168, 170, 176, 177, 195, 199, 203, 204, 205, 206, 207, 215, 224, 225, 229, 233, 235, 274, 279, 288, 301, 307, 308, 322, 343, 358, 360, 362, 365, 366, 367, 370, 383, 384, 385, 386, 391, 393, 395, 397, 408 and 414.

These positions are characterized in that mutagenesis of the enzyme at these positions lead to an improvement in the desired enzyme characteristics.

Preferred mutations include:
A22T, E23K, E23Q, E24D, M28L, K46E, K46R, D53K, D53N, D57Y, G67R, G74R, E75K, E75V, V77I, S78T, E79V, Q82H, Q82K, Q82R, F88Y, N95D, N95P, N96P, N96S, N96Y, Q97T, T98G, T98P, S101F, P102L, G103E, V105I, A109T, D112V, D112Y, F122Y, L126I, Y136N, E140V, K142R, T143I, T143P, N148D, K151G, M152K, M152V, T154I, S156T, L160F, K161N, N164D, E168D, A170T, L176Q, L176V, Y177F, S195T, T199I, T203I, T203L, T203S, T203W, E204A, E204G, E204H, E204I, E204N, E204R, E204V, K205P, K205R, S206R, S206T, T207A, T207S, L215F, D224H, N225D, N225E, P229S, S233C, S235A, Q274H, Q274L, Q279E, R288M, L301S, E307Y, N308D, N308T, A322V, G343A, K358R, K360N, T362A, T362I, N365D, T366S, D367N, Q370H, D383V, I384F, I384L, I384M, Q385R, P386Q, K391N, A393P, K395T, D397N, S408I and L414I or conservative mutations at each position.

By "conservative mutations" is meant mutations to amino acid residues that are conservative in terms of the amino acid characteristics compared to the amino acid residue indicated. Amino acid characteristics include the size of the residue, hydrophobicity, polarity, charge, pK-value, and other amino acid characteristics known in the art and also described in more detail below.

In a particularly preferred embodiment, the mutations are at one or more of the following positions: 23, 46, 53, 75, 82, 88, 95, 96, 98, 112, 143, 152, 176, 177, 199, 203, 204, 205, 225, 229, 233, 274, 288, 307, 308, 362, 370, 384 and 385

Preferred mutations at these specific positions include:
E23K, E23Q, K46E, K46R, D53K, D53N, E75K, E75V, Q82H, Q82K, Q82R, F88Y, N95D, N95P, N96P, N96S, N96Y, T98G, D112V, D112Y, T143I, T143P, M152K, M152V, L176Q, L176V, Y177F, T199I, T203I, T203L, T203S, T203W, E204A, E204G, E204H, E204I, E204N, E204R, E204V, K205P, K205R, N225D, N225E, P229S, S233C, Q274H, Q274L, R288M, E307Y, N308D, N308T, T362A, T362I, Q370H, I384F, I384L, I384M and Q385R or conservative mutations at each position.

In one embodiment, there is provided a phytase comprising one mutation selected from the group consisting of:
P229S; D112V; Q82R; Q274H; D112Y; F88Y; K46E; S233C; R288M; I384L; Q385R; Q274L; E307Y; T199I; Q82K and T203I.

In a further preferred embodiment, there is provided a phytase comprising a combination of mutations selected from the group consisting of:
K46E/Q82H; Q82K/V105I; N148D/T362I; K46E/L414I; F88Y/Y136N; T154I/P386Q; N95P/N96S; N95P/N96P; Q97T/T98G; D224H/N225E; Y177F/T199I; Q274L/Q370H; K46E/N96Y; N148D/L301S; E24D/R288M; E140V/A322V; K46E/S195T; E75K/N365D; T98P/S235A; L160F/L215F; Q274L/K395T; G67R/Q279E/N308T; K161N/P229S/R288M; D53N/D57Y/M1±52V; F122Y/S156T/P229S; T199I/S206R/T207S; E23K/K46E/Q82H; K46E/Q82H/Q385R; T203W/E204N/K205R; T203W/E204H/K205R; T203W/E204R/K205R; T203W/E204A/K205R; A22T/K151G/N308D; E23K/E75K/F88Y; M152K/N225D/L301S; S78T/Q274L/S408I; L176Q/T199I/T366S; K46E/V77I/T203 S; K46R/T199I/D367N; G74R/E204G/R288M; A22T/T199I/S206T/T207A; Q82R/F88Y/L126I/I384L; K46E/Q82H/E 168D/Q274L; Q82K/T154I/Q279E/N308T; Q82R/D112V/Q274H/T362A; E24D/E79V/N95D/K360N; E23K/M28L/A109T/T143P/I384L; D53N/D57Y/T199I/P229S/R288M; K46E/Q82H/N148D/T154I/T362I; D53N/D57Y/P229S/1R288M/K358R; D53N/D57Y/T154I/P229S/R288M; Y136N/T199I/T203L/E204I/K205P; E23Q/S101F/Q274L/I384M/K391N; K46E/Q82H/N95D/D112V/K142R/D383V; D53N/D57Y/M152V/P229S/R288M/A393P; D53K/D57Y/M152V/P229S/R288M/A393P; D53N/D57Y/F88Y/M152V/P229S/Q279E/N308T; D53N/D57Y/M152V/E204V/P229S/R288M/A393P; D53N/D57Y/M152V/T154I/P229S/R288M/A393P; D53N/D57Y/Q82H/G103E/M152V/P229S/R288M/A393P; K46E/D53N/D57Y/T143I/M152V/L176V/P229S/R288M/A393P; Q82K/F88Y/N96P/Q97T/T98G/V105I/Q274H/Q279E/A393P; Q82R/F88Y/N95P/N96P/Q97T/Q279E/I384L/P386Q/A393P; H18Q/D53N/D57Y/E75V/M152V/A170T/P229S/R288M/Q385R/A393P; Q82K/F88Y/N96P/T98G/Y136N/M152V/Y177F/T362I/I384F/A393P/D397N; D53N/D57Y/F88Y/N95P/N96P/V105I/D112V/Y136N/N148D/N164D/Q274H/T362I/I384L/A393P; D53N/D57Y/Q82K/F88Y/N95P/P102L/V105I/Y136N/N148D/Y177F/Q274H/Q279 E/T362I/A393P, and; D53N/D57Y/Q82K/F88Y/N96P/T98G/V105I/D112V/Y177F/Q274L/G343A/T362I/I384L/A393P.

In a yet further preferred embodiment, there is provided a phytase comprising a combination of mutations selected from the group consisting of:
D57Y/F88Y/N95P/Q97T/N148D/M152V/T154I/Y177F/Q274H/I384L; D53N/D57Y/F88Y/N95P/N96P/Q97T/M152V/Y177F/Q274H/Q279E/T362I/I384L; D53N/Q82K/F88Y/N96P/T98G/V105I/N148D/T154I/Q274H/T362I/I384L/P386Q; Q82R/F88Y/N96P/T98G/V105I/D112V/Y136N/N148D/T154I/Y177F/P386Q/A393P; D53N/Q82K/F88Y/N95P/N96P/T98G/Y136N/N148D/T154I/I384L/P386Q/A393P; D57Y/Q82K/F88Y/N96P/Q97T/T98G/V105I/N148D/T154I/Y177F/Q274H/I384L/P 386Q/A393P; D53N/Q82K/F88Y/N95P/Q97T/T98G/D112V/Y136N/N148D/T154I/Q274H/Q279E/I384L/P386Q/A393P and D53N/D57Y/Q82R/F88Y/N95P/N96P/Q97T/T98G/V105I/Y136N/N148D/M152V/Y 177F/I384L/P386Q.

Accordingly, a preferred phytase in accordance with the present invention is a variant consisting of the amino acid sequence listed as SEQ ID NO: 3 and having one or more of the amino acid mutations listed above or one of the combinations of mutations listed above.

In these embodiments, the nomenclature indicates a phytase comprising the amino acid sequence set out in SEQ ID NO: 3 with the mutations indicated by reference to the positions of the amino acids in SEQ ID NO: 3. The nomenclature is described in more detail below.

Suitably these variants show improved characteristics with respect to any one of the following: temperature stability, pH range, pepsin stability, specific activity, substrate specificity. Suitable methods for determining these characteristics are disclosed herein.

In particular, the improvements in phytase characteristics are directed to the enzyme stability under food and feed processing conditions, to the enzyme stability during stomach transit, and to the enzyme activity and stability in human or animal stomach and/or intestinal tract making the improved variants particularly suitable for use as feed supplements. Thus, such improvements comprise among other parameters the increase in stability at elevated temperatures, preferably at temperatures above 65° C., the increase in stability against proteolytic digestion, preferably protease of the digestive tract, the increase in catalytic activity at low pH, preferably catalytic activity below pH 5.5, and the general efficiency of releasing phosphate groups from phytate.

Suitably, in one embodiment, the phytase or functional equivalent of the present invention is characterised in that said phytase has a specific activity of 1000 U/mg or higher wherein said specific activity is determined by incubating said phytase in a solution containing 2 mM phytate, 0.8 mM $CaCl_2$ in 200 mM sodium acetate buffer at pH 3.5. In another embodiment, the phytase of the present invention or functional equivalent thereof may also suitably be characterised in that said phytase has two activity maxima around pH 3 and pH 4-4.5 wherein said activity is determined by incubating said phytase in a solution containing 2 mM phytate, 0.8 mM $CaCl_2$ in 200 mM sodium acetate buffer.

In a further embodiment the invention provides a method of preparing a phytase enzyme variant, which method comprises:
a) Selecting a parent phytase enzyme, wherein the parent phytase enzyme is selected from
i. a parent phytase enzyme with at least 75% homology to SEQ ID No 3
ii. a parent phytase enzyme derived from *Citrobacter* spp.
b) Making at least one alteration which is an insertion, a deletion or a substitution of an amino acid residue in the parent phytase enzyme to obtain a phytase enzyme variant
c) Screening for a phytase enzyme variant which compared to the parent phytase enzyme has:
i. higher thermal stability and/or
ii. specific activity and/or
iii. proteolytic stability and/or
d) Preparing the phytase enzyme variant In a further embodiment the invention provides a method of preparing a phytase enzyme variant, which method comprises:
a) Subjecting DNA sequence encoding a parent phytase enzyme to mutagenesis, wherein the parent phytase enzyme is selected from
i. a parent phytase enzyme with at least 75% homology to SEQ ID No 3
ii. a parent phytase enzyme derived from *Citiobacter* spp.
b) Expressing the mutated DNA sequence obtained in step (A) in a host cell, and
c) Screening for host cells expressing a for a phytase enzyme variant which compared to the parent phytase enzyme has:
iv. higher thermal stability and/or
v. higher specific activity* and/or
vi. higher proteolytic stability and/or
Preparing the phytase enzyme variant expressed by the host cell In the above embodiments of the invention, which relate to methods of preparing phytase enzyme variant the phytase enzyme variant is preferably screened for higher thermal stability.

In the above embodiments of the invention, which relate to methods of preparing phytase enzyme variant the phytase enzyme variant is preferably screened for higher thermal stability and higher proteolytic stability.

In the above embodiments of the invention, which relate to methods of preparing phytase enzyme variant the phytase enzyme variant is preferably screened for higher thermal stability and higher proteolytic stability and higher specific activity.

The parent phytase enzyme is preferably derived from *Citrobacter freundii*, more preferably *Citrobacter freundii* P3-42.

In methods of preparing a phytase enzyme variant, which method comprises subjecting DNA sequence encoding a parent phytase enzyme to mutagenesis, the DNA sequence encoding a parent phytase enzyme is preferably subjected to random mutagenesis, more preferably error prone PCR, even more preferably error threshold PCR.

The preferred methods of mutagenesis of DNA sequence encoding a parent phytase enzyme is error prone PCR, more preferably error threshold PCR, other methods of mutagenesis may be used either in place of error prone/threshold PCR or in conjunction with error prone/threshold PCR. See Example 12 which provides references for suitable error prone PCR and error threshold PCR methods. Other methods are disclosed under the The term 'expression in a host cell' when used in the context of the embodiments which refer to 'a method of preparing a phytase enzyme variant' is preferably defined as production of the phytase enzyme variant in a living organism, organ or cell as herein defined. However, it is considered that for the purpose of selection the phytase enzyme variants may also be produced via in vitro methods which utilise the transcription and translation machinery isolated from of one or more cells isolated from one or more living organism. Such in vitro production of variant phytases on the invention can also be used for selecting preferred variant phytases. In vitro expression can suitable performed using standard techniques. For reference please see 'In vitro Expression Guide' available from Promega Inc (Part# BR053).

Definitions of Variant Phenotypes.

Variants with higher thermal stability (thermal stability difference) is preferably determined using the methods disclosed in Example 12.

The variant phytase enzyme prepared by the method of preparing phytase enzyme variants preferably has a thermal stability difference of at least 1.5, more preferably 2, 2.5, 3, 3.5, 4, 5, 6, 7, 8, 9, most preferably at least 10.

Variants with higher proteolytic stability is preferably determined by the methods disclosed in Example 12.

Preferably the phytase enzyme variant of the invention has a proteolytic stability of at least 45%, preferably 50%, 55%, more preferably at least 60%.

Further Variant Embodiments

In a further embodiment the invention provides methods for the preparation of an animal feed comprising a phytase enzyme variant.
a) Selecting a parent phytase enzyme, wherein the parent phytase enzyme is selected from
i. a parent phytase enzyme with at least 75% homology to SEQ ID No 3
ii. a parent phytase enzyme derived from *Citrobacter* spp.
b) Making at least one alteration which is an insertion, a deletion or a substitution of an amino acid residue in the parent phytase enzyme to obtain a phytase enzyme variant
c) Screening for a phytase enzyme variant which compared to the parent phytase enzyme has:
i. higher thermal stability and/or
ii. specific activity and/or
iii. proteolytic stability and/or
d) Preparing the phytase enzyme variant
e) Adding the prepared phytase enzyme variant to an animal feed.

In a further embodiment the invention provides methods for the preparation of an animal feed comprising a phytase enzyme variant.
a) Subjecting DNA sequence encoding a parent phytase enzyme to mutagenesis,
wherein the parent phytase enzyme is selected from
iii. a parent phytase enzyme with at least 75% homology to SEQ ID No 3
iv. a parent phytase enzyme derived from *Citrobacter* spp.
b) Expressing the mutated DNA sequence obtained in step (A) in a host cell, and
c) Screening for host cells expressing a for a phytase enzyme variant which compared to the parent phytase enzyme has:
vii. higher thermal stability and/or
viii. higher specific activity* and/or
ix. higher proteolytic stability and/or
d) Preparing the phytase enzyme variant expressed by the host cell
f) Adding the prepared phytase enzyme variant to an animal feed.

The preferred aspects of the method of preparing a phytase enzyme variant also apply to the above methods of preparing an animal feed comprising a phytase enzyme variant.

In another aspect, the invention provides an isolated and/or purified nucleic acid molecule or nucleotide sequence coding for the enzyme comprising the amino acid sequence corresponding to *Citrobacter freundii* phytase, or a homologue thereof. Suitably said isolated and/or purified nucleic acid molecule encodes a polypeptide comprising the amino acid sequence as shown in SEQ ID NO: 3 or a sequence having at least 75% identity (homology) thereto or an effective fragment thereof. In one embodiment, the nucleic acid molecule encodes a polypeptide comprising SEQ ID NO:3 and including mutations at the preferred positions listed herein or any of the specific mutations or combinations of mutations listed herein. In another embodiment, the invention provides an isolated and/or purified nucleic acid molecule comprising a nucleotide sequence that is the same as, or is complementary to, or contains any suitable codon substitutions for any of those of SEQ ID NO: 2 or comprises a sequence which has at least 75%, 80%, 85%, 90%, 95%, 96%, 97%, 98% or 99% sequence homology with SEQ ID NO: 2.

In a yet further aspect, the invention relates to a nucleotide sequence and to the use of a nucleotide sequence shown as:

(a) the nucleotide sequence presented as SEQ ID No.2,
(b) a nucleotide sequence that is a variant, homologue, derivative or fragment of the nucleotide sequence presented as SEQ ID No. 2;
(c) a nucleotide sequence that is the complement of the nucleotide sequence set out in SEQ ID No. 2;
(d) a nucleotide sequence that is the complement of a variant, homologue, derivative or fragment of the nucleotide sequence presented as SEQ ID No 2;
(e) a nucleotide sequence that is capable of hybridising to the nucleotide sequence set out in SEQ ID No. 2;
(f) a nucleotide sequence that is capable of hybridising to a variant, homologue, derivative or fragment of the nucleotide sequence presented as SEQ ID No. 2;
(g) a nucleotide sequence that is the complement of a nucleotide sequence that is capable of hybridising to the nucleotide sequence set out in SEQ ID No. 2;
(h) a nucleotide sequence that is the complement of a nucleotide sequence that is capable of hybridising to a variant, homologue, derivative or fragment of the nucleotide sequence presented as SEQ ID No. 2;
(i) a nucleotide sequence that is capable of hybridising to the complement of the nucleotide sequence set out in SEQ ID No.2;
(j) a nucleotide sequence that is capable of hybridising to the complement of a variant, homologue, derivative or fragment of the nucleotide sequence presented as SEQ ID No. 2.

The nucleotide sequence of the present invention may comprise sequences that encode for SEQ ID No. 3 or a variant, modified form, homologue or derivative thereof.

In particular, the invention provides a plasmid or vector system comprising a phytase as described herein or a homologue or derivative thereof. Preferably, the plasmid or vector system comprises a nucleic acid sequence as set out in SEQ ID No: 2 or a sequence that is at least 75% homologous thereto or an effective fragment thereof. Suitably the plasmid or vector system is an expression vector for the expression of any of the enzymes encoded by a nucleic acid sequence as set out in any of SEQ ID No: 2 or a sequence that is at least 75% homologous (identical) thereto in a microorganism. In addition, the invention provides a plasmid or vector system for expression of any of the modified enzymes or variants described herein. Suitable expression vectors are described herein.

In another aspect of the invention there is provided a host cell transformed or transfected with a nucleic acid encoding a phytase as described herein.

Suitably, the host cell in accordance with this aspect of the invention comprises a phytase which comprises an amino acid sequence, or functional fragment thereof, as set out in SEQ ID NO: 3 or a sequence that is at least 75% homologous thereto.

In a preferred embodiment, said host cell produces a phytase.

In a further aspect of the invention there is provided a host cell transformed or transfected with a nucleic acid encoding a phytase in accordance with the invention. Preferably, the phytase is a *Citrobacter freundii* phytase as described herein or a homologue or derivative thereof. Suitably, said phytase enzyme comprises an amino acid sequence, or functional fragment thereof, as set out in any of SEQ ID No: 3 or a sequence that is at least 75% homologous (identical) thereto. Preferably, said host cell produces a phytase.

In one embodiment, the nucleotide sequence which can be used in the present invention is obtainable from (though it does not have to be actually obtained from) *Citrobacter fre-*

*undii*, although it will be recognised that enzymes isolated and/or purified from equivalent strains may equally be used.

Suitably the host cell is derived from a microorganism including bacteria and fungi, including yeast. In a particularly preferred embodiment the host cell is a prokaryotic bacterial cell. Suitable bacterial host cells include bacteria from different prokaryotic taxonomic groups including proteobacteria, including members of the alpha, beta, gamma, delta and epsilon subdivision, gram-positive bacteria such as Actinomycetes, Firmicutes, Clostridium and relatives, flavobacteria, cyanobacteria, green sulfur bacteria, green non-sulfur bacteria, and archaea. Particularly preferred are the Enterobacteriaceae such as *Escherichia coli* proteobacteria belonging to the gamma subdivision and low GC-Gram positive bacteria such as *Bacillus*.

Suitable fungal host cells include yeast selected from the group consisting of Ascomycota including Saccharomycetes such as *Pichia, Hansenula*, and *Saccharomyces, Schizosaccharmycetes* such as *Schizosaccharonzyces pombe* and anamorphic Ascomycota including *Aspergillus*.

Other suitable eukaryotic host cells include insect cells such as SF9, SF21, Trychplusiani and M121 cells. For example, the polypeptides according to the invention can advantageously be expressed in insect cell systems. As well as expression in insect cells in culture, phytase genes can be expressed in whole insect organisms. Virus vectors such as baculovirus allow infection of entire insects. Large insects, such as silk moths, provide a high yield of heterologous protein. The protein can be extracted from the insects according to conventional extraction techniques. Expression vectors suitable for use in the invention include all vectors which are capable of expressing foreign proteins in insect cell lines.

Other host cells include plant cells selected from the group consisting of protoplasts, cells, calli, tissues, organs, seeds, embryos, ovules, zygotes, etc. The invention also provides whole plants that have been transformed and comprise the recombinant DNA of the invention.

The term "plant" generally includes eukaryotic alga, embryophytes including Bryophyta, Pteridophyta and Spermatophyta such as Gymnospermae and Angiospermae.

Preferably, said host cell is a microorganism. Preferred microorganisms include prokaryotic bacterial cells preferably, *E. coli, B. subtilis* and other species of the genus *Bacillus*, yeast, preferably, *Hansenula polymorpha* and *Schizosaccharomyces pombe*.

In another aspect of the invention there is provided a bacterial cell strain *Citrobacter freundii* P3-42 deposited by Danisco Global Innovation, Sokeritehtaantie 20, FIN-02460 Kantvik, Finland under accession number NCIMB 41247. Such a cell can be incorporated directly into feed.

In another aspect, there is provided a method for the production of phytases comprising transfecting a host cell with an expression vector or plasmid in accordance with the invention, culturing said host cell under conditions for the expression of the phytase and extracting said phytase from the host cell culture media.

Suitably said method is for the production of a phytase comprising expressing an amino acid sequence as set out in SEQ ID NO: 3 or a sequence having at least 75% homology thereto or an effective fragment thereof in a host cell and extracting the secreted protein from the host cell culture medium.

Another aspect of the invention provides a feed composition comprising a phytase in accordance with the invention. Preferably, the feed composition comprises a phytase at a concentration of 10-10000 U/kg feed, preferably, 200-2000 U/kg feed, more preferably, 500-1000 U/kg feed.

In one embodiment, the feed composition comprises a host cell in accordance with the invention.

In a further aspect there is provided the use of a phytase in accordance with the invention in food or animal feed.

Preferable Aspects

Preferable aspects are presented in the accompanying claims and in the following description and Examples section.

Additional Advantages

The present invention is advantageous as it provides phytases that have a number of properties that make them particularly useful as additives to animal feeds.

In particular, the phytases of the present invention are active at low pH and, preferably in the range pH 2 to 5.5 with activity maxima around pH 3 and 4.5. Suitably the phytases of the present invention are active at low pHs of the stomach environment.

Furthermore, the phytases of the present invention are efficiently secreted both in the native host and during heterologous expression thus leading to more efficient production and isolation for addition to feed.

Moreover, the phytases of the present invention have a broad substrate specificity including penta-tetra, tri and di-phosphate substrates thereby increasing the total available phosphate to the animal. The phytases of the present invention also have a high specific activity in the region of 1000 U/mg +/− approximately 10%.

The products of the present invention may be used as additives/supplements to foods and feed. The products may also be useful in the commercial production of various inositol-phosphates.

Phytate/Phytic Acid/Phytases

Phytic acid (myo-inositol hexakisphosphate) is an important constituent in cereals, legumes and oilseed crops. The salt form, phytate, is the major storage form of phosphorous in these plants.

Phytases catalyse phosphate monoester hydrolysis of phytic acid which results in the step-wise formation of myo-inositol pentakis-, tetrakis-, tris-, bis- and monophosphates, as well as the liberation of inorganic phosphate.

The terms "wild type phytase" or "wild type" as used herein refer to a phytase enzyme with an amino acid sequence found in nature.

The terms "phytase variant" or "variant" or "modified form" refer to a phytase enzyme with an amino acid sequence derived from the amino acid sequence of a parent phytase having one or more amino acid substitutions, insertions, and/or deletions, which together are referred to as "mutations".

The terms "parent phytase" or "parent enzyme" refer to a phytase enzyme from which a phytase variant is derived. A parent phytase can be a wild type phytase or another phytase variant. In particular, in the present invention, a "parent phytase" may be derived from a *Citrobacter freundii*. Suitably, the "parent phytase" is derived from *Citrobacter freundii* strain P3-42 as described herein which, preferably has the amino acid sequence set out in SEQ ID NO:3.

Isolated

In one aspect, preferably the nucleotide or amino acid sequence is in an isolated form. The term "isolated" means that the sequence is at least substantially free from at least one other component with which the sequence is naturally associated in nature and as found in nature.

Purified

In one aspect, preferably the nucleotide or amino acid sequence is in a purified form. The term "purified" means that the sequence is in a relatively pure state—e.g. at least about 90% pure, or at least about 95% pure or at least about 98% pure.

Nucleotide Sequence

The scope of the present invention encompasses nucleotide sequences encoding enzymes having the specific properties as defined herein.

The term "nucleotide sequence" as used herein refers to an oligonucleotide sequence, nucleic acid or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" or "nucleic acid molecule" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Preparation of a Nucleotide Sequence

Typically, the nucleotide sequence encompassed by scope of the present invention or the nucleotide sequences for use in the present invention are prepared using recombinant DNA techniques (i.e. recombinant DNA). However, in an alternative embodiment of the invention, the nucleotide sequence could be synthesised, in whole or in part, using chemical methods well known in the art (see Caruthers M H et al, (1980) *Nuc Acids Res Symp Ser* 215-23 and Horn T et al., (1980) *Nuc Acids Res Symp Ser* 225-232).

A nucleotide sequence encoding either an enzyme which has the specific properties as defined herein or an enzyme which is suitable for modification may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for the enzyme (e.g. maltose for a glucosidase (maltase) producing enzyme), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence however, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Molecular Evolution

Once an enzyme-encoding nucleotide sequence has been isolated and/or purified, or a putative enzyme-encoding nucleotide sequence has been identified, it may be desirable to modify the selected nucleotide sequence, for example it may be desirable to mutate the sequence in order to prepare an enzyme having improved stability characteristics in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984)2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence.

Thus, it is possible to produce numerous site directed or random mutations into a nucleotide sequence, either in vivo or in vitro, and to subsequently screen for improved functionality of the encoded polypeptide by various means.

As a non-limiting example, mutations or natural variants of a polynucleotide sequence can be recombined with either the wildtype or other mutations or natural variants to produce new variants. Such new variants can also be screened for improved functionality of the encoded polypeptide. The production of new preferred variants may be achieved by various methods well established in the art, for example the Error Threshold Mutagenesis (WO 92/18645), oligonucleotide mediated random mutagenesis (U.S. Pat. No. 5,723,323), DNA shuffling (U.S. Pat. No. 5,605,793), exo-mediated gene assembly (WO 0058517), or RCR® Recombination Chain Reaction (EP 1230390 and U.S. Pat. No. 6,821,758). Other suitable methods are described, for example in WO 0134835, WO 02/097130, WO 03/012100, WO03/057247, WO 2004/018674, U.S. Pat. No. 6,303,344 and U.S. Pat. No. 6,132,970.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate Amino Acid Sequences The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The enzyme encompassed in the present invention may be used in conjunction with other enzymes. Thus the present invention also covers a combination of enzymes wherein the combination comprises the enzyme of the present invention and another enzyme, which may be another enzyme according to the present invention. This aspect is discussed in a later section.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Variants/Homologues/Derivatives

The present invention also encompasses the use of variants, homologues and derivatives of any amino acid sequence of an enzyme or of any nucleotide sequence encoding such an enzyme.

Here, the term "homologue" means an entity having a certain homology with the amino acid sequences and the nucleotide sequences. Here, the term "homology" can be equated with "identity". Suitably, "homologous" in this context refers to the percentage of sequence identity between two enzymes after aligning their sequences using alignment algorithms as described in more detail below.

In the present context, a homologous amino acid sequence is taken to include an amino acid sequence which may be at least 75, 80, 81, 85 or 90% identical, preferably at least 95, 96, 97, 98 or 99% identical to the sequence. Typically, the homologues will comprise the same active sites etc.—e.g. as the subject amino acid sequence. Although homology can also be considered in terms of similarity (i.e. amino acid residues having similar chemical properties/functions), in the context of the present invention it is preferred to express homology in terms of sequence identity.

By "functional fragment" is meant a fragment of the polypeptide that retains that characteristic properties of that polypeptide. In the context of the present invention, a functional fragment of a phytase enzyme is a fragment that retains the carotenoid cleavage capability of the whole protein.

In the present context, an homologous nucleotide sequence is taken to include a nucleotide sequence which may be at least 75, 80, 81, 85 or 90% identical, preferably at least 95, 96, 97, 98 or 99% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

For the amino acid sequences and the nucleotide sequences, homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 *Short Protocols in Molecular Biology*, 4$^{th}$ Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756)(Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| SET | | SUB-SET | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The present invention also encompasses conservative or homologous substitutions or mutations (substitution and replacement are both used herein to mean the interchange of an existing amino acid residue, with an alternative residue) that may occur, i.e. like-for-like substitution. Thus, the term "conservative mutation" refers to an amino acid mutation that a person skilled in the art would consider conservative to a first mutation. "Conservative" in this context means conserving or invariable in terms of the amino acid characteristics. If, for example, a mutation leads at a specific position to a substitution of an aromatic amino acid residue (e.g. Tyr) with an aliphatic amino acid residue (e.g. Leu) then a substitution at the same position with a different aliphatic amino acid (e.g. Ile or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc.

Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

Nomenclature

In the present invention, the conventional one-letter and three-letter codes for amino acid residues are used. For ease of reference, mutations in enzyme variants are described by use of the following nomenclature: amino acid residue in the parent enzyme; position; substituted amino acid residue(s). According to this nomenclature, the substitution of, for instance, an alanine residue for a glycine residue at position 20 is indicated as Ala20Gly or A20G. The deletion of alanine in the same position is 1035 shown as Ala20* or A20*. The insertion of an additional amino acid residue (e.g. a glycine) is indicated as Ala20AlaGly or A20AG. The deletion of a consecutive stretch of amino acid residues (e.g. between alanine at position 20 and glycine at position 21) is indicated as Δ(Ala20-Gly21) or Δ(A20-G21). When a parent enzyme sequence contains a deletion in comparison to the enzyme sequence used for numbering an insertion in such a position (e.g. an alanine in the deleted position 20) is indicated as *20Ala or *20A. Multiple mutations are separated by a plus sign or a slash. For example, two mutations in positions 20 and 21 substituting alanine and glutamic acid for glycine and serine, respectively, are indicated as A20G+E21S or A20G/E21S. When an amino acid residue at a given position is substituted with two or more alternative amino acid residues these residues are separated by a comma or a slash. For example, substitution of alanine at position 30 with either glycine or glutamic acid is indicated as A20G,E or A20G/E, or A20G, A20E. When a position suitable for modification is identified herein without any specific modification being suggested, it is to be understood that any amino acid residue may be substituted for the amino acid residue present in the position. Thus, for instance, when a modification of an alanine in position 20 is mentioned but not specified, it is to be understood that the alanine may be deleted or substituted for any other amino acid residue (i.e. any one of R,N,D,C,Q,E,G,H,I,L,K,M,F,P,S,T,W,Y,V).

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Biologically Active

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

In particular, variant sequences or modified forms thereof have a similar enzymatic profile to the profile of the phytase identified herein. This profile includes characteristics such as being a secreted protein, having a pH optimum in the range of pH 2 to 5.5, preferably 3.0 to 3.5, retaining at least 50% of the maximum activity over the pH range 2.0-5.5 and/or having a specific activity over 1000 U/mg.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 50° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

Site-Directed Mutagenesis

Once an enzyme-encoding nucleotide sequence has been isolated and/or purified, or a putative enzyme-encoding nucleotide sequence has been identified, it may be desirable to mutate the sequence in order to prepare an enzyme of the present invention.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151). A further method is described in Sarkar and Sommer (*Biotechniques* (1990), 8, p 404-407—"The megaprimer method of site directed mutagenesis").

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression of Enzymes

The nucleotide sequence for use in the present invention may be incorporated into a recombinant replicable vector. The vector may be used to replicate and express the nucleotide sequence, in enzyme form, in and/or from a compatible host cell.

Expression may be controlled using control sequences e.g. regulatory sequences.

The enzyme produced by a host recombinant cell by expression of the nucleotide sequence may be secreted or may be contained intracellularly depending on the sequence and/or the vector used. The coding sequences may be designed with signal sequences which enhance direct secretion of the substance coding sequences through a particular prokaryotic or eukaryotic cell membrane.

Advantageously, the enzymes of the present invention are secreted.

Expression Vector

The terms "plasmid", "vector system" or "expression vector" means a construct capable of in vivo or in vitro expression. In the context of the present invention, these constructs may be used to introduce genes encoding enzymes into host cells. Suitably, the genes whose expression is introduced may be referred to as "expressible transgenes".

Preferably, the expression vector is incorporated into the genome of a suitable host organism. The term "incorporated" preferably covers stable incorporation into the genome.

The nucleotide sequences described herein including the nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB 110, pE194, pAMB1, pIJ702 and pET11.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of an enzyme having the specific properties as defined herein or in the methods of the present invention.

Thus, a further embodiment of the present invention provides host cells transformed or transfected with a nucleotide sequence that expresses the enzymes described in the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the enzyme of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

The genotype of the host cell may be modified to improve expression.

Examples of host cell modifications include protease deficiency, supplementation of rare tRNA's, and modification of the reductive potential in the cytoplasm to enhance disulphide bond formation.

For example, the host cell *E. coli* may overexpress rare tRNA's to improve expression of heterologous proteins as exemplified/described in Kane (*Curr Opin Biotechnol* (1995), 6, 494-500 "Effects of rare codon clusters on high-level expression of heterologous proteins in *E. coli*"). The host cell may be deficient in a number of reducing enzymes thus favouring formation of stable disulphide bonds as exemplified/described in Bessette (*Proc Natl Acad Sci USA* (1999), 96, 13703-13708 "Efficient folding of proteins with multiple disulphide bonds in the *Escherichia coli* cytoplasm").

In one embodiment, host cells in the context of the present invention include those cells that can be added directly into animal feed.

Organism

The term "organism" in relation to the present invention includes any organism that could comprise the nucleotide sequence coding for the enzymes as described in the present invention and/or products obtained therefrom, and/or wherein a promoter can allow expression of the nucleotide sequence according to the present invention when present in the organism.

Suitable organisms may include a prokaryote, fungus, yeast or a plant.

The term "transgenic organism" in relation to the present invention includes any organism that comprises the nucleotide sequence coding for the enzymes as described in the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the enzymes as described in the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the enzyme of the present invention under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillis subtilis.*

Teachings on the transformation of prokaryotic hosts is well documented in the art, for example see Sambrook et al (Molecular Cloning: A Laboratory Manual, 2nd edition, 1989, Cold Spring Harbor Laboratory Press). Other suitable methods are set out in the Examples herein. If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger.*

A transgenic *Aspergillus* according to the present invention can also be prepared by following, for example, the teachings of Turner G. 1994 (Vectors for genetic manipulation. In: Martinelli S. D., Kinghorn J. R.(Editors) *Aspergillus:* 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit. Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature, London,* 275, 104); and Ito, H et al (1983, J Bacteriology 153, 163-168).

The transformed yeast cells may be selected using various selective markers—such as auxotrophic markers dominant antibiotic resistance markers.

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Culturing and Production

Host cells transformed with the nucleotide sequence of the present invention may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme.

The protein produced by a recombinant cell may be displayed on the surface of the cell.

The enzyme may be secreted from the host cells and may conveniently be recovered from the culture medium using well-known procedures.

Secretion

It may be desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the α-factor gene (yeasts e.g. *Sacchaaromyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Other suitable assays for detecting phytase activity are known in the art and exemplified herein.

Fusion Proteins

The amino acid sequence for use according to the present invention may be produced as a fusion protein, for example to aid in extraction and purification. Examples of fusion protein partners include glutathione-S-transferase (GST), 6×His, GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence. Gene fusion expression systems in *E. coli* have been reviewed in *Curr Opin Biotechnol* (1995) 6(5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Additional Sequences

The sequences for use according to the present invention may also be used in conjunction with one or more additional proteins of interest (POIs) or nucleotide sequences of interest (NOIs).

Non-limiting examples of POIs include: Xylanase, lipases, acid phosphatases and/or others. These include enzymes that, for example, modulate the viscosity of the feed. The NOI may even be an antisense sequence for any of those sequences.

The POI may even be a fusion protein, for example to aid in extraction and purification or to enhance in vivo phytate metabolism.

The POI may even be fused to a secretion sequence.

Other sequences can also facilitate secretion or increase the yield of secreted POI. Such sequences could code for chaperone proteins as for example the product of *Aspergillus niger* cyp B gene described in UK patent application 9821198.0.

The NOI coding for POI may be engineered in order to alter their activity for a number of reasons, including but not limited to, alterations, which modify the processing and/or expression of the expression product thereof. By way of further example, the NOI may also be modified to optimise expression in a particular host cell. Other sequence changes may be desired in order to introduce restriction enzyme recognition sites.

The NOI coding for the P01 may include within it synthetic or modified nucleotides—such as methylphosphonate and phosphorothioate backbones.

The NOI coding for the POI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

Antibodies

One aspect of the present invention relates to amino acids that are immunologically reactive with the amino acid of SEQ ID No. 3.

Antibodies may be produced by standard techniques, such as by immunisation with the substance of the invention or by using a phage display library.

For the purposes of this invention, the term "antibody", unless specified to the contrary, includes but is not limited to, polyclonal, monoclonal, chimeric, single chain, Fab fragments, fragments produced by a Fab expression library, as well as mimetics thereof. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. Furthermore, the antibodies and fragments thereof may be humanised antibodies. Neutralising antibodies, i.e., those which inhibit biological activity of the substance polypeptides, are especially preferred for diagnostics and therapeutics.

If polyclonal antibodies are desired, a selected mammal (e.g., mouse, rabbit, goat, horse, etc.) is immunised with the sequence of the present invention (or a sequence comprising an immunological epitope thereof). Depending on the host species, various adjuvants may be used to increase immunological response.

Serum from the immunised animal is collected and treated according to known procedures. If serum containing polyclonal antibodies to the sequence of the present invention (or a sequence comprising an immunological epitope thereof) contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against the sequence of the present invention (or a sequence comprising an immunological epitope thereof) can also be readily produced by one skilled in the art and include, but are not limited to, the hybridoma technique Koehler and Milstein (1975 *Nature* 256:495-497), the human B-cell hybridoma technique (Kosbor et al., (1983) *Immunol Today* 4:72; Cote et al., (1983) *Proc Natl Acad Sci* 80:2026-2030) and the EBV-hybridoma technique (Cole et al., (1985) *Monoclonal Antibodies and Cancer Therapy*, Alan Rickman Liss Inc, pp 77-96).

In addition, techniques developed for the production of "chimeric antibodies", the splicing of mouse antibody genes to human antibody genes to obtain a molecule with appropriate antigen specificity and biological activity may be used (Morrison et al., (1984) *Proc Natl Acad Sci* 81:6851-6855; Neuberger et al., (1984) *Nature* 312:604-608; Takeda et al., (1985) *Nature* 314:452-454).

Alternatively, techniques described for the production of single chain antibodies (U.S. Pat. No. 4,946,779) can be adapted to produce the substance specific single chain antibodies.

Antibody fragments which contain specific binding sites for the substance may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al., (1989) *Science* 256:1275-128 1).

Large Scale Application

In one preferred embodiment of the present invention, the amino acid sequence encoding a *C. freundii*-derived phytase or the methods of the present invention are used for large scale applications. In particular, the methods of the present invention may be used for the large scale production of phytases for industrial use as additives/supplements to food or feed compositions.

Preferably the amino acid sequence is produced in a quantity of from 5 g per litre to about 10 g per litre of the total cell culture volume after cultivation of the host organism.

Preferably the amino acid sequence is produced in a quantity of from 100 mg per litre to about 900 mg per litre of the total cell culture volume after cultivation of the host organism.

Preferably the amino acid sequence is produced in a quantity of from 250 mg per litre to about 500 mg per litre of the total cell culture volume after cultivation of the host organism.

Use of Phytases

As stated above, the present invention also relates to the production of phytases as described herein.

In particular, the present invention also relates to the use of the amino acid sequences as disclosed herein in the production of organic and inorganic phosphate compounds.

Thus, the present invention further relates to the use of the nucleotide sequences encoding phytases in generating expression vectors or systems for the expression of the phytases.

In addition, the present invention relates to the use of such expression vectors or systems in the generation of host cells which express phytases.

The invention further relates to the use of modified host cells in the generation of precursors of organic and inorganic phosphate compounds or in the generation of specific organic phosphate compounds.

Suitable organic and inorganic phosphate compounds include myo-inositol pentakis-, tetrakis-, tris-, bis- and mono-phosphates.

Suitably, the invention therefore provides a method of producing an organic phosphate compound comprising treating a phytate with a phytase derived from *Citrobacter freundii*. Preferably, the method is characterised in that the enzyme comprises the amino acid sequences shown as SEQ ID NOs: 3 or a sequence having at least 75% identity (homology) thereto or an effective fragment, or modified form thereof.

Suitably, the organic phosphate is phytate or all possible stereoisomers of myo-inositol di-, tri-, tetra, and pentaphosphates. Other suitable organic phosphates include inositol-tetraphosphates and inositol-oligophosphates. In a preferred embodiment, the method is an in vivo biotechnological process.

Such methods for producing an organic phosphate compound may suitably comprise the steps of:
a) providing a host cell that comprises expressible transgenes comprising *C. freundii* phytase;
b) culturing the transgenic organism under conditions suitable for expression of the transgene; and
c) recovering the organic phosphate compound from the culture.

The compounds can be used for a number of applications including in assays for the characterisation of phytases. Some inositol phosphates are involved as signal molecules in intracellular regulation and can be used research chemicals.

In another aspect there is provided a method for production of food or animal feed. Animal feed is typically produced in feed mills in which raw materials are first ground to a suitable particle size and then mixed with appropriate additives. The feed may then be produced as a mash or pellets; the later typically involves a method by which the temperature is raised to a target level and then the feed is passed through a die to produce pellets of a particular size. Subsequently liquid additives such as fat and enzyme may be added. The pellets are allowed to cool prior to transportation. Production of animal feed may also involve an additional step that includes extrusion or expansion prior to pelleting.

Accordingly, the invention further provides the use of an amino acid sequence encoding a phytase or a host cell expressing a phytase to produce a phytase for use in the manufacture of a food or feed product. In one aspect, there is provided a use of an amino acid sequence as described herein in the manufacture of a food or feed product. In another aspect, there is provided a use of a host cell in accordance with the invention in the manufacture of a food or feed product. In another aspect, there is provided a use of an expression vector or system in accordance with the invention in the manufacture of a food or feed product.

The present invention also covers using the enzymes as a component of feed combinations with other components to deliver to animals.

Combination with Other Components

The enzymes of the present invention may be used in combination with other components or carriers.

Suitable carriers for feed enzymes include wheat (coarsely ground). In addition there are a number of encapsulation techniques including those based on fat/wax coverage, adding plant gums etc.

Examples of other components include one or more of: thickeners, gelling agents, emulsifiers, binders, crystal modifiers, sweetners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions.

As used herein the term "binder" refers to an ingredient (e.g. a food ingredient) that binds the product together through a physical or chemical reaction.

The term "crystal modifier" as used herein refers to an ingredient (e.g. a food ingredient) that affects the crystallisation of either fat or water.

"Carriers" or "vehicles" mean materials suitable for compound administration and include any such material known in the art such as, for example, any liquid, gel, solvent, liquid diluent, solubiliser, or the like, which is non-toxic and which does not interact with any components of the composition in a deleterious manner.

Examples of nutritionally acceptable carriers include, for example, grain, water, salt solutions, alcohol, silicone, waxes, petroleum jelly, vegetable oils, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

As used herein the term "component suitable for animal or human consumption" means a compound which is or can be added to the composition of the present invention as a supplement which may be of nutritional benefit, a fibre substitute or have a generally beneficial effect to the consumer.

By way of example, the components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

Food or Feed Substance

The compounds may be used as—or in the preparation of—a food or feed substance. Here, the term "food" is used in a broad sense—and covers food and food products for humans as well as food for animals (i.e. a feed). The term "feed" is used with reference to products that are fed to animals in the rearing of livestock. In a preferred aspect, the food or feed is for consumption by monogastric animals such as pig, poultry and fish.

The food or feed may be in the form of a solution or as a solid—depending on the use and/or the mode of application and/or the mode of administration.

Food and Feed Ingredients and Supplements

The compounds may be used as a food or feed ingredient.

As used herein the term "food or feed ingredient" includes a formulation, which is or can be added to foods or foodstuffs and includes formulations which can be used at low levels in a wide variety of products.

The food ingredient may be in the form of a solution or as a solid—depending on the use and/or the mode of application and/or the mode of administration.

The compounds may be—or may be added to—food supplements.

Foods and Feed Compositions

Feed compositions for monogastric animals typically include compositions comprising plant products which contain phytate. Such compositions include cornmeal, soybean meal, rapeseed meal, cottonseed meal, maize, wheat, barley and sorghum-based feeds.

The phytases described herein may be—or may be added to—foods or feed compositions.

The present invention also provides a method of preparing a food or a feed ingredient or supplement, the method comprising admixing phytases produced by the process of the present invention or the composition according to the present invention with another food ingredient. The method for preparing or a food ingredient is also another aspect of the present invention. Methods for preparing animal feed are set out above. The enzyme can be added also in the form of a solid formulation, or as a feed additive, such as a pre-mix. A solid form is typically added before or during the mixing step; and a liquid form is typically added after the pelleting step.

Pharmaceutical

The phytases of the present invention may also be used in pharmaceutical preparations or for combination into food stuffs in order to provide some pharmaceutical effect. For example, EP 1,389,915 describes the use of a phytase in a food or drink for increasing the availability of Calcium, Iron and/or Zinc of the food or drink for humans.

In addition, EP 1,392,353 describes a medicament or nutritional supplement containing phytase, which is useful for increasing bioavailability of bioelements, e.g., calcium and iron, and for combating deficiency diseases.

Here, the term "pharmaceutical" is used in a broad sense—and covers pharmaceuticals and/or nutraceuticals for humans as well as pharmaceuticals and/or nutraceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

When used as—or in the preparation of—a pharmaceutical, the product and/or the compounds of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid—depending on the use and/or the mode of application and/or the mode of administration.

Pharmaceutical Ingredient

The product and/or the compounds of the present invention may be used as pharmaceutical ingredients. Here, the product and/or the composition of the present invention may be the sole active component or it may be at least one of a number (i.e. 2 or more) active components.

The pharmaceutical ingredient may be in the form of a solution or as a solid—depending on the use and/or the mode of application and/or the mode of administration.

The pharmaceutical ingredient may be in the form of an effervescent product to improve the dissolving properties of the pharmaceutical.

Forms

The product and/or the compounds of the present invention may be used in any suitable form—whether when alone or when present in a composition. Likewise, phytases produced in accordance with the present invention (i.e. ingredients—such as food ingredients, functional food ingredients or pharmaceutical ingredients) may be used in any suitable form.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the product and/or the composition are used in a tablet form—such as for use as a functional ingredient—the tablets may also contain one or more of: excipients, disintegrants, granulation binders, or lubricating agents.

Examples of nutritionally acceptable carriers for use in preparing the forms include, for example, water, salt solutions, alcohol, silicone, waxes, petroleum jelly and the like.

Preferred excipients for the forms include lactose, starch, a cellulose, milk sugar or high molecular weight polyethylene glycols.

For aqueous suspensions and/or elixirs, carotenoid cleavage compounds may be combined with various sweetening or flavouring agents, colouring matter or dyes, with emulsifying and/or suspending agents and with diluents such as water, ethanol, propylene glycol and glycerin, and combinations thereof.

The forms may also include gelatin capsules; fibre capsules, fibre tablets etc.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual, Second Edition*, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

EXAMPLES

The invention is now further illustrated in the following non-limiting examples.

Example 1

Phytase Activity Assay

Phytase assays were carried out in microtitre plates. The reaction mixture (100 µl) contained: 2 mM phytate and 0.8 mM $CaCl_2$ in 200 mM sodium acetate buffer, pH 3.5. The reaction was allowed to proceed for 1 h at 37° C. after which time the released phosphate was measured by a modification of a known procedure (Heinonen J. K., Lahti R. J. Anal Biochem. 113 (2), 313-317 (1981)). Briefly, 200 µl of a freshly prepared AMM solution (7.5 N $H_2SO_4$, 15 mM ammonium molybdate and acetone–1:1:2) was added to the 100 µl reaction mixture in each microtitre plate well. The absorbance at 390 nm was measured not earlier than 10 min and not later than 30 min after addition of the AMM reagent. The amount of phosphate was determined by building a calibration curve with phosphate solutions of known concentrations. For assaying phytase activity at different pH values the following (all 200 mM) buffers were used: glycine/HCl between pH 2.0 and 3.0, sodium acetate/acetic acid between pH 3.5 and 5.5, Tris/maleic acid between pH 6.0 and 7.5.

Example 2

Phytase-Producing Strain P3-42

Bacterial strain P3-42 was originally isolated from a mass of decaying birch leaves collected in a wet forest in southern Finland. The strain can be aerobically cultivated at 30° C. on many simple culture media e.g. LB (1% peptone, 0.5% yeast extract, 1% NaCl, pH 7.4) or low phosphate medium PP1 (1% peptone, 1%, beef extract, 0.5%, yeast extract, $CaCl_2$-0.2M. The medium is adjusted to pH 11 with NaOH and boiled for 10 min. The precipitate is removed by filtration, pH re-adjusted to 5.5 and the medium sterilised by autoclaving for 15 min at 121° C.).

After growth in liquid PP1 medium the strain was found to exhibit phytase activity both at pH 3.5 and 5.5 (assayed as described in Example 1). The ratio of activities at 3.5 and 5.5 was about 1.5. The activity was also measured separately in the cells and culture supernatant of P3-42. According to these measurements about 90% of all phytase activity was found in supernatant. The strain was deposited with NCIMB on 22 Sep. 2004 under accession number NCIMB 41247.

Example 3

Isolation of Chromosomal DNA from the Strain P3-42

Chromosomal DNA was prepared essentially by the standard procedure (Ausubel et al., *Current Protocols in Molecular Biology*, John Wiley & Sons, New York, 1996). A 250 ml culture grown overnight at 30° C. in LB medium was centrifuged at 10,000 rpm for 30 min, washed in 20 ml of 50 mM tris-HCl, 5 mM EDTA pH 8 and re-suspended in 10 ml of cold TES (50 mM tris-HCl, 5 mM EDTA, 15% glucose pH 8). Lysozyme was added to 10 mg/ml, and the cell suspension was incubated at 37° C. for 30-60 min until lysis occurred, ascertained for by dilution of 100 µl of the reaction mixture into 1 ml of 1% SDS and checking for a "slimy" consistency. At this time, SDS and Proteinase K (Sigma) were added to a final concentration of 1% and 0.5 mg/ml respectively. The reaction mixture was incubated for 30 min at 56° C. followed by addition of 2 ml of 5 M NaCl and 1.4 ml 10% cetyltrimethylammonium bromide (Sigma). The incubation was continued for 15 min 65° C. The solution was extracted once with chloroform/isoamyl alcohol (24:1) and once with phenol/chloroform. After the extractions, the water phase was mixed with 0.6 vol of isopropanol, the DNA precipitate collected by centrifugation (10,000 rpm, 15 min), washed with 70% ethanol, vacuum dried and re-suspended in 2 ml of 10 mM tris-HCl, 1 mM EDTA pH 8, 5 µg/ml. RNAse.

Example 4

Taxonomic Identification of the Bacterial Strain P3-42

A fragment of the 16S rRNA gene of the strain P3-42 was amplified by the polymerase chain reaction (PCR) with Taq DNA polymerase (Roche) using the primers; 536f (CAGC-MGCCGCGGTAATWC) (SEQ ID No. 4) and 1392r (ACGGGCGGTGTGTRC) (SEQ ID No. 5), (Lane, D. J. In Nucleic acid techniques in bacterial systematics, Stackbrandt, E. and Goodfellow, M. eds, John Wiley & Sons, New York: pp 115-117 (1991)). The following program was used: 1) initial DNA denaturation step of 5 min at 95° C.; 2) 30 cycles of 1 min at 94° C., 1 min at 55° C., 1 min at 72° C.; 3) a final extension step of 70° C. for 10 min. The PCR products, approximately 900 base pairs in size, were purified by electrophoresis in a 0.8% agarose gel and extracted from the gel using a PCR Purification Kit (Qiagen) according to the manufacturer's instructions. The purified PCR products were sequenced by Medprobe (Norway) as a commercial service. The sequenced area is listed as SEQ ID No 1. This sequence was compared to DNA sequences in the GenBank database (http://www.ncbi.nlm.nih.gov/blast/). The highest match (823 out of 824 nucleotides, 99.9%) was found with the sequence of 16S RNA gene from *Citrobacter freundii* DSM 30039. Therefore, strain P3-42 can be taxonomically classified as *Citrobacter freundii*.

Example 5

Cloning of the Phytase Gene from *C. freundii* P3-42

Chromosomal DNA from the *Citrobacter freundii* strain P3-42 was partially digested with restriction endonuclease Sau3A and the digest fractionated on 1% agarose gel. The DNA fragments of 3 to 5 kb were isolated from the gel using a gel purification kit (Qiagen) and ligated with BamHI digested dephosphorylated A-ZAP arms (Stratagene). Subsequent steps for library construction followed the instructions of Stratagene's ZAP Express Predigested Vector/Gigapack Cloning Kit. The phage form of the library was converted into a plasmid form by the "mass excision" procedure as described by the manufacturer (Stratagene). Screening of plasmid library was done by similarly to the earlier published methods for the detection of phytase activity on Petri plates (Howson and Davis. Enzyme Microb. Technol. 5, 377-382 (1983); Chen J. C. Biotechnology techniques 12 (10) 751-761 (1998); Riccio M. L. et al, J. Appl. Microbiol. 82, 177-185 (1997)). Several phytase-positive clones were isolated and purified by sub-cloning. These isolates were grown in liquid culture (LB medium at 30° C. and 200 rpm for about 24 h) and phytase activity was measured (Example 1) in the resulting cell suspensions. One clone that had the highest phytase activity (about 5 U/ml at pH 3.5) was selected for subsequent characterisation. Plasmid DNA was isolated this clone, named pBK(P3-42) and characterised by partial DNA sequencing of the insert DNA (sequencing service was obtained from Medprobe (Norway). This sequence comprising the phytase gene is listed as SEQ ID No: 2. The deduced amino acid sequence of the *C. freundii* phytase is listed as SEQ ID No: 3. Comparison of the SEQ ID No: 3 with the sequences in GenBank using the BLAST service provided by NCBI identifies the phytase from *E. coli* as the closest known homologue of the *C. freundii* phytase. However, the level homology is low—only about 62% of amino acid residues are identical in both proteins.

Example 6

Amplification and Expression of Phytase Gene from *C. freundii* P3-42

Phytase gene was amplified by PCR. Chromosomal DNA of the strain *C. freundii* P3-42 was used as template and oligonucleotides o42-5 (GGAATTCATATGAGTACAT-TCATCATTCG) (SEQ ID No. 6) and o42-3 (GGAATTCG-GATCCCTTATTCCGTAACTGCACAC) (SEQ ID No. 7) as primers. The amplification was carried out using the Expand High Fidelity PCR System kit (Roche). The following program was used: 1) initial DNA denaturation for 3 min at 94° C.; 2) 35 cycles of 45 sec at 94° C., 45 sec at 55° C., 1 min at 68° C., 1 min at 72° C., 1 min at 74° C.; 3) a final extension step of 10 min at 72° C. The resulting PCR product was purified by electrophoresis in a 0.8% agarose gel followed by DNA extraction from the gel using a Gel Purification Kit (Qiagen). The purified PCR product was digested with the restriction enzymes NdeI and BamHI and isolated from the reaction mixture by the PCR Purification Kit (Qiagen). The vector plasmid pET11a (Novagen) was digested with the restriction endonucleases NdeI and BamHI, de-phosphorylated using shrimp alkaline phosphatase (Roche) and purified by electrophoresis in a 0.8% agarose gel. The linearised plasmid DNA band was excised from the gel and purified using a Gel Purification Kit (Qiagen). The two purified DNA fragments were ligated using T4 DNA ligase (Roche). The ligation reaction was precipitated with 70% ethanol, washed with ethanol and re-suspended directly into 50 µl of electrocompetent *E. coli* XL1-Blue MRF' cells. The suspension was transferred to a 0.1 cm electroporation cuvette (BioRad) and electroporated using a Gene Pulser Xcell (BioRad) set at 1800 V, 25 µF and 200Ω. Immediately after electroporation 1 ml of LB medium was added, the cell suspension was transferred to a 15 ml plastic tube (Falcon) and incubated at 37° C. with shaking (200 rpm) for 1 hr. The transformed cells were plated onto LB plates containing 100 .mu·g/ml ampicillin and incubated overnight at 37.degree. C. 24 transformants were grown in liquid culture and the cultures used for assaying phytase activity and isolation of plasmid DNA. One clone producing highest phytase activity and generating the expected restriction pattern of the plasmid DNA was selected. The plasmid contained by this clone named pET11(P3-42) was used to transform the expression host strain BL21 (DE3) pLysS (Novagen). The transformed cell suspension, was shaken for 1 h at 37° C. in LB containing 2% glucose and inoculated into 50 ml of LB containing ampicillin (100 µg/ml) and glucose (2%) and grown overnight at 30° C. with shaking (200 rpm). The OD of the resulting culture was measured at 600 nm and the culture was used to inoculate 1 l of LB+ampicillin (100 µg/ml) to an $OD_{600}$ of 0.04. Growth was continued overnight at 30° C. The phytase activity in such cultures was typically 50-60 U/ml (measured at pH 3.5). Almost all of the phytase was secreted into the culture medium. The fact that *C. freundii* phytase is an efficiently secreted enzyme both in its native host and in during heterologous expression in *E. coli* is in contrast to the intracellular nature of a phytase from *C. brakii* (Kim H. W. et al. Biotechnol. Lett. 25, 1231-1234 (2003)). The activity in the culture of a control strain BL21-(DE3)pLysS transformed with pET 1 grown under the same conditions was below 0.05 U/ml.

Example 7

Purification of the Recombinant Phytase from C. freundii P3-42

The culture of BL21(DE3)pLysS transformed with pET11 (P3-42) was centrifuged to remove the bacterial cells, concentrated using a rotary evaporator to about 1/10 of the original volume and dialysed against water until the conductivity of the solution decreased below 250 µS/cm. The pH of the solution was adjusted to 8.0 with tris base and it was applied to a column (3×20 cm) of DEAE Sepharose Fast Flow (Amersham Biosciences) equilibrated with 25 mM tris-HCl, pH 8.0. The column was washed with the equilibration buffer at a flow rate of 3 ml/min for 30 min followed by elution with three successive gradients of NaCl in 25 mM tris-HCl, pH 8.0: 0-50 mM, 50-150 mM and 150-500 mM. Each of the three gradients was programmed for 1 h with a constant flow rate of 3 ml/min. 9 ml fractions were collected and assayed for phytase activity. One strong peak of activity was detected. The protein in the peak fraction was concentrated using Centriplus concentrators (Amicon) and analysed SDS PAGE using a 12% gel and the standard Laemmli buffer system. The results of this analysis indicated that the preparation of recombinant C. freundii P3-42 phytase obtained by DEAE Sepharose contains a single prominent protein component. Semi-quantitative analyses based on scanning of the digital image of the gel (FIG. 1) indicate the purity of about 60-70%.

Example 8 pH Profile of the Recombinant Phytase from C. freundii P3-42

Figure 2:
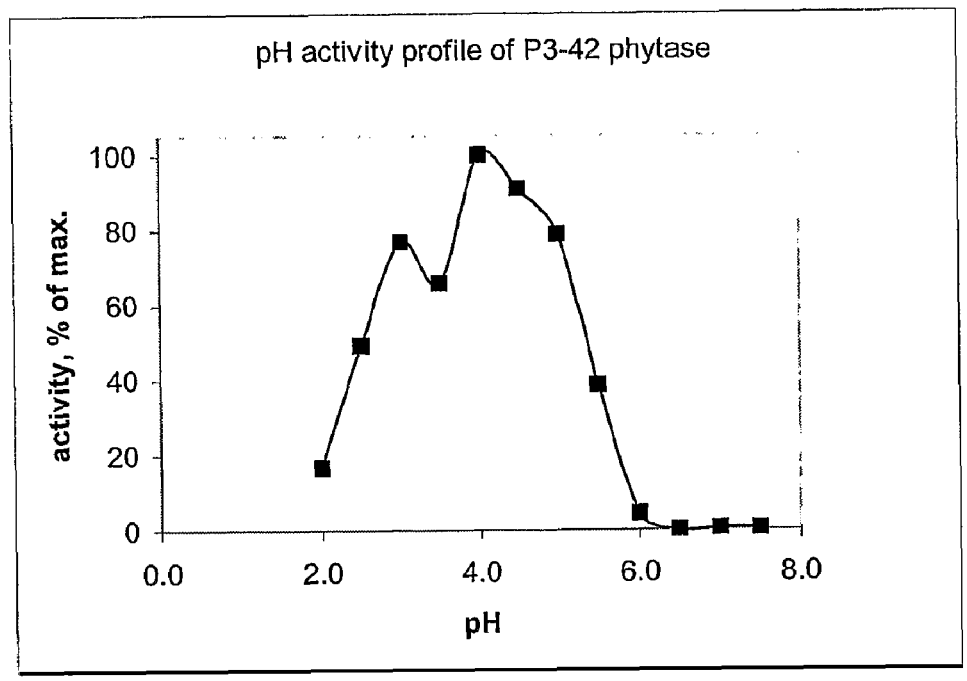
FIG. 2 shows pH profile of the phytase from *C. freundii* P3-42

Dependence of the activity of the C. freundii P3-42 phytase from (purified according to the Example 7) on pH was studied in buffers and under conditions described in Example 1. The enzyme was active in a broad pH area (2-5.5) with two activity maxima around pH 3 and 4-4.5 (FIG. 2).

Example 9

Substrate Specificity of the Recombinant Phytase from C. freundii P3-42

Figure 3:
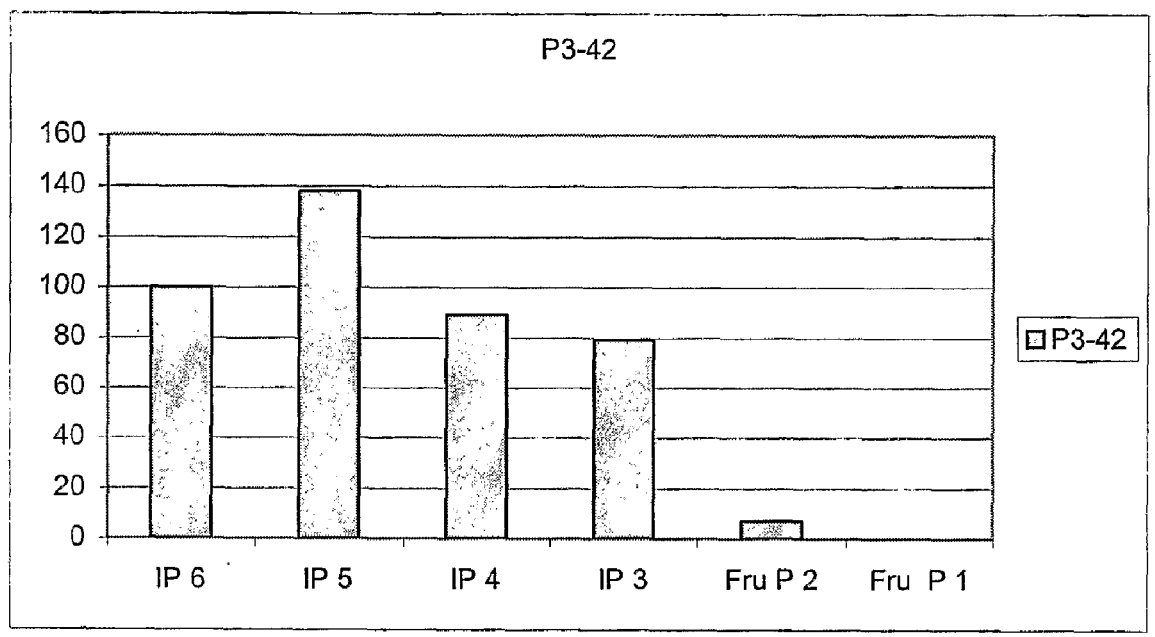
FIG. 3 shows substrate specificity of the purified recombinant phytase from *C. freundii* P3-42 with inositol phosphate fractions of different degree of phosphorylation and model substrates. Abbreviations: IP6—phytic acid, IP5, IP4 and IP3— mixtures of isomeric inositol penta-, tetra- and triphosphates respectively. Fru P2-fructose 1,6-diphosphate, Fru P1-fructose 6-phosphate.

The fractions of inositol phosphates containing three, four or five phosphates per inositol residue were isolated by ion-exchange chromatography from a partial hydrolysate of phytic acid treated with fungal phytase (Natuphos). Production and purification of these preparations was a commercial service of BioChemis Ltd (St. Petersburg, Russia). Contamination of each fraction with inositol-phosphates having a different degree of phosphorylation was less that 5% as judged by HPLC (Sandberg A. S., Ahderinne R. J. Food Sci. 51 (3), 547-550). Commercial fructose 1,6-diphosphate and fructose 6-phosphate (Sigma) were used as model substrates used to estimate the specificity of the C. freundii P3-42 phytase towards di- and monophosphate substrates. The activity of the C. freundii phytase purified according to the Example 7 with different substrates was measured by the standard assay (Example 1) at pH 3.5 using 2 mM concentrations of substrates in the final reaction mixture. The results (FIG. 3) indicate that that the enzyme has maximum activity with inositol pentaphosphate. Activities with inositol tri- and tetraphosphates as well as phytic acid were rather similar while fructose 1,6-diphosphate was a rather poor substrate. Hydrolysis of fructose 6-phosphate was below reliable detection limit.

Example 10

Specific Activity of the Recombinant Phytase from C. freundii P3-42

Specific activity of the C. freundii phytase was estimated using the purified preparation according to the Example 7. The phytase activity was measured at pH 3.5 according to the Example 1. Phytase concentration was calculated by measuring total protein concentration with BCA Protein Assay Kit (Pierce) and correcting it by phytase content estimated by SDS PAGE (Example 7). According to these measurements, the specific activity of the recombinant phytase from C. freundii P3-42 is about 1100 U/mg.

Example 11

Comparison of C. freundii P3-42 Phytase with the Phytase from C. brakii YH-15

The only phytase from a bacterium belonging to the Citrobacter family described earlier is the intracellular phytase from C. brakii YH-15 (Kim H. W. et al. Biotechnol. Lett. 25, 1231-1234 (2003)). This enzyme shares some properties with the secreted phytase of C. freundii of the present invention both enzymes are acid phytases of high specific activity. Direct comparison of the amino acid sequences of the two enzymes is impossible because the sequence information regarding the C. brakii enzyme is limited to a stretch of 10 amino acid residues. The deduced amino acid sequence of C. freundii phytase contains a fragment sharing 9 out of 10 residues with the sequence from C. brakii enzymes. However, comparison of such short fragments of sequence does not allow any conclusions about the overall homology of the two enzymes to be made. The most striking difference between the two enzymes is in cellular location: while the enzyme from C. brakii is intracellular, the C. freundii phytase is clearly a secreted enzyme. The enzyme is secreted in its native host, its deduced amino acid sequence does contain a signal peptide (as predicted by the Signal P algorithm: http://www.cbs.dtu.dk/services/SignalP/), the enzyme is also very efficiently secreted from E. coli under its native signal peptide. In addition to that, there are a number of significant differences in biochemical properties of the two enzymes (Table 1). Table 1
Comparison of the Phytase from C. freundii P3-42 with phytase from C. brakii YH-14

| Property | C. brakii YH-15 phytase | C. freundii P3-42 phytase |
|---|---|---|
| Localisation | Intracellular | Secreted |
| Specific Activity | 3457 U/mg (pH 4) | 1100 U/mg (pH 3.5) |
| pH optimum | 4.0 | 3.0, 5.0 |
| Thermostability | 20%(*) | 58% |

(*)Measured under conditions described by Kim et al. (Biotechnol. Lett. 25, 1231-1234 (2003)): heat treatment in 100 mM Na acetate, pH 4, 60° C., 30 min followed by standard assay at 37° C.

Example 12

Generation and Characterisation of Phytase Variants

Phytase variants were constructed by mutagenesis of the sequence SEQ ID No. 2 using mutagenesis methods as listed above such as the methods disclosed in Morinaga et al (Biotechnology (1984)2, p 646-649), or in Nelson and Long (Analytical Biochemistry (1989), 180, p 147-151), or the Error Threshold Mutagenesis protocol described in WO 92/18645.

Phytase enzyme variants were characterized after heterologous expression in one or more of the following expression hosts: *Escherichia coli* K12; *Bacillus subtilis*; *Saccharomyces cerevisiae*.

1. Thermostability

The thermostability of the variants was characterized by the inactivation temperature of the enzyme. The inactivation temperature was determined by measuring the residual activity of the enzyme in an enzyme assay as described in Example 1 after incubation for 10 min at different temperatures and subsequent cooling to room temperature. The inactivation temperature is the temperature at which the residual activity is 50% compared to the residual activity after incubation for the same duration under the same conditions at room temperature. Where appropriate interpolations and extrapolations from the measured activity data are done in order to determine the temperature corresponding to 50% residual activity. Thermostability differences in ° C. were calculated by subtracting the inactivation temperatures of two enzymes from each other. (i.e. Thermostability difference (T.D.) is compared to parent phytase (=inactivation temperature (variant)−inactivation temperature parent))

Table 2 lists the thermostability differences for different variants:

TABLE 2

Thermostability differences for variants derived from the parent phytase P3-42 having the sequence shown in Seq ID No 3.

| Variant | T.D. |
|---|---|
| P229S | 1.5 |
| D112V | 1.5 |
| Q82R | 1.5 |
| Q274H | 1.0 |
| D112Y | 2.5 |
| F88Y | 1.5 |
| K46E | 2.0 |
| S233C | 2.0 |
| R288M | 4.0 |
| I384L | 1.0 |
| Q385R | 1.5 |
| Q274L | 2.0 |
| E307Y | 1.0 |
| T199I | 2.0 |
| Q82K | 2.0 |
| T203I | 1.0 |
| K46E/Q82H | 2.5 |
| Q82K/V105I | 1.0 |
| N148D/T362I | 1.5 |
| K46E/L414I | 1.0 |
| F88Y/Y136N | 1.0 |
| N95P/N96S | 1.5 |
| N95P/N96P | 2.0 |
| Q97T/T98G | 1.0 |
| Y177F/T199I | 2.5 |
| Q274L/Q370H | 3.0 |
| K46E/N96Y | 2.5 |
| N148D/L301S | 1.5 |
| E24D/R288M | 1.5 |
| E140V/A322V | 2.0 |
| K46E/S195T | 2.0 |
| E75K/N365D | 1.5 |
| T98P/S235A | 2.0 |
| L160F/L215F | 1.0 |
| Q274L/K395T | 1.5 |
| G67R/Q279E/N308T | 2.0 |
| K161N/P229S/R288M | 2.0 |
| D53N/D57Y/M152V | 2.0 |
| F122Y/S156T/P229S | 1.5 |
| E23K/K46E/Q82H | 6.0 |
| K46E/Q82H/Q385R | 5.0 |

TABLE 2-continued

Thermostability differences for variants derived from the parent phytase P3-42 having the sequence shown in Seq ID No 3.

| Variant | T.D. |
|---|---|
| T203W/E204N/K205R | 2.0 |
| T203W/E204H/K205R | 3.0 |
| T203W/E204R/K205R | 3.0 |
| T203W/E204A/K205R | 3.0 |
| A22T/K151G/N308D | 2.0 |
| E23K/E75K/F88Y | 2.0 |
| M152K/N225D/L301S | 2.0 |
| S78T/Q274L/S408I | 2.0 |
| L176Q/T199I/T366S | 1.5 |
| K46E/V77I/T203S | 3.0 |
| K46R/T199I/D367N | 1.5 |
| G74R/E204G/R288M | 1.5 |
| A22T/T199I/S206T/T207A | 1.5 |
| Q82R/F88Y/L126I/I384L | 3.0 |
| K46E/Q82H/E168D/Q274L | 5.0 |
| Q82K/T154I/Q279E/N308T | 5.5 |
| Q82R/D112V/Q274H/T362A | 5.0 |
| E24D/E79V/N95D/K360N | 1.0 |
| E23K/M28L/A109T/T143P/I384L | 2.0 |
| D53N/D57Y/T199I/P229S/R288M | 6.0 |
| K46E/Q82H/N148D/T154I/T362I | 7.0 |
| D53N/D57Y/P229S/R288M/K358R | 5.5 |
| D53N/D57Y/T154I/P229S/R288M | 7.0 |
| Y136N/T199I/T203L/E204I/K205P | 3.0 |
| E23Q/S101F/Q274L/I384M/K391N | 2.0 |
| K46E/Q82H/N95D/D112V/K142R/D383V | 5.5 |
| D53N/D57Y/M152V/P229S/R288M/A393P | 7.0 |
| D53N/D57Y/M152V/P229S/R288M/A393P | 8.0 |
| D53N/D57Y/F88Y/M152V/Q279E/N308T | 6.5 |
| D53N/D57Y/M152V/E204V/P229S/R288M/A393P | 8.0 |
| D53N/D57Y/M152V/T154I/P229S/R288M/A393P | 8.0 |
| D53N/D57Y/Q82H/G103E/M152V/P229S/R288M/A393P | 8.5 |
| K46E/D53N/D57Y/T143I/M152V/L176V/P229S/R288M/A393P | 8.0 |
| Q82K/F88Y/N96P/Q97T/T98G/V105I/Q274H/Q279E/A393P | 9.0 |
| Q82R/F88Y/N95P/N96P/Q97T/Q279E/I384L/P386Q/A393P | 9.0 |
| D53N/D57Y/E75V/M152V/A170T/P229S/R288M/Q385R/A393P | 7.5 |
| Q82K/F88Y/N96P/T98G/Y136N/M152V/Y177F/T362I/I384F/A393P/D397N | 10.0 |
| D53N/D57Y/F88Y/N95P/N96P/V105I/D112V/Y136N/N148D/N164D/Q274H/T362I/I384L/A393P | 10.0 |
| D53N/D57Y/Q82K/F88Y/N95P/P102L/V105I/Y136N/N148D/Y177F/Q274H/Q279E/T362I/A393P | 10.0 |
| D53N/D57Y/Q82K/F88Y/N96P/T98G/V105I/D112V/Y177F/Q274L/G343A/T362I/I384L/A393P | 9.0 |

2. Other Characteristics

Other characteristics were also improved.

Thermostability, specific activity, and pepsin stability of selected variants were compared using assays as described above. The pepsin stability of such variants was characterized by residual activities measured at pH 3.5, 37° C. after pepsin incubation compared to control conditions (residual activity=activity after pepsin incubation/activity after incubation under control conditions). The pepsin incubation was performed for 2 hours at pH 2.0, 0.25 mg/ml pepsin, 1 mM $CaCl_2$ and 5 mg/ml BSA at 37° C. Control conditions were 2 hours at pH 5.0, 1 mM $CaCl_2$ and 5 mg/ml BSA at 37° C.

TABLE 3 shows properties of selected variants (derived from and compared to wt phytase according to Seq ID No. 3).

| Variant | T.D. [° C.] | Specific activity [% of wt activity] | Pepsin stability [% residual activity] (wt = 41%) |
|---|---|---|---|
| K46E/Q82H | 2.2 | 96 | 65 |

Sequence Information

SEQ ID No: 1
CGATTACTAGCGATTCCGACTTCTGGAGTCGAGTTGCAGACTCCAATCCG

GACTACGACATACTTTATGAGGTCCGCTTGCTCTCGCGAGGTCGCTTCTC

TTTGTATATGCCATTGTAGCACGTGTGTAGCCCTACTCGTAAGGGCCATG

ATGACTTGACGTCATCCCCACCTTCCTCCAGTTTATCACTGGCAGTCTCC

TTTGAGTTCCCGGCCGAACCGCTGGCAACAAAGGATAAGGGTTGCGCTCG

TTGCGGGACTTAACCCAACATTTCACAACACGAGCTGACGACAGCCATGC

AGCACCTGTCTCAGAGTTCCCGAAGGCACCAAAGCATCTCTGCTAAGTTC

TCTGGATGTCAAGAGTAGGTAAGGTTCTTCGCGTTGCATCGAATTAAACC

ACATGCTCCACCGCTTGTGCGGGCCCCCGTCAATTCATTTGAGTTTTAAC

CTTGCGGCCGTACTCCCCAGGCGGTCGACTTAACGCGTTAGCTCCGGAAG

CCACGCCTCAAGGGCACAACCTCCAAGTCGACATCGTTTACGGCGTGGAC

TACCAGGGTATCTAATCCTGTTTGCTCCCCACGCTTTCGCACCTGAGCGT

CAGTCTTTGTCCAGGGGGCCGCCTTCGCCACCGGTATTCCTCCAGATCTC

TACGCATTTCACCGCTACACCTGGAATTCTACCCCCCTCTACAAGACTCT

AGCCTGCCAGTTTCGGATGCAGTTCCCAGGTTGAGCCCGGGCATTTCACA

TCCGACTTGACAGACCGCCTGCGTGCGCTTTACGCCCAGTAATTCCGATT

AACGCTTGCACCCTCCGTATTAC

SEQ ID No 2:
AAAGGTGGTGCTGGTAATGAGTACATTCATCATTCGTTTATTATTTTTTT

CTCTCTTATGCGGTTCTTTCTCAATACATGCTGAAGAGCCGAACGGTATG

AAACTTGAGCGGGTTGTGATAGTGAGCCGTCATGGAGTAAGAGCACCTAC

GAAGTTCACTCCAATAATGAAAGATGTTACACCCGATCAATGGCCACAAT

GGGATGTGCCGTTAGGATGGCTAACGCCTCGTGGGGAGAACTTGTTTCT

GAATTAGGTCAGTATCAACGTTTATGGTTCACAAGCAAAGGTCTGTTGAA

TAATCAAACGTGCCCATCTCCAGGGCAGGTTGCTGTTATTGCAGACACGG

ATCAACGCACCCGTAAAACGGGTGAGGCGTTTCTGGCTGGGTTAGCACCA

AAATGTCAAATTCAAGTGCATTATCAGAAGGATGAAGAAAAAACTGATCC

TCTTTTTAATCCAGTAAAAATGGGGACATGTTCGTTTAACACATTGAAGG

TTAAAAACGCTATTCTGGAACGGGCCGGAGGGAAATATTGAACTGTATACC

CAACGCTATCAATCTTCATTTCGGACCCTGGAAAATGTTTTAAATTTCTC

ACAATCGGAGACATGTAAGACTACAGAAAAGTCTACGAAATGCACATTAC

CAGAGGCTTTACCGTCTGAACTTAACGTAACTCCTGACAATGTATCATTA

CCTGGTGCCTGGAGTCTTTCTTCCACGCTGACTGAGATATTTCTGTTGCA

AGAGGCCCAGGGAATGCCACAGGTAGCCTGGGGCGTATTACGGGAGAAA

AAGAATGGAGAGATTTGTTAAGTCTGCATAACGCTCAGTTTGATCTTTTG

CAAAGAACTCCAGAAGTTGCCCGTAGTAGGGCACACCATTACTCGATAT

GATAGACACTGCATTATTGACAAATGGTACAACAGAAACAGGTATGGCA

TAAAATTACCCGTATCTCTGTTGTTTATTGCTGGTCATGATACCAATCTT

GCAAATTTAAGCGGGCTTTAGATCTTAACTGGTCGCTGCCCGGTCAACC

CGATAATACCCCTCCTGGTGGGGAGCTTGTATTCGAAAAGTGGAAAAGAA

CCAGTGATAATACGGATTGGGTTCAGGTTTCATTTGTTTATCAGACGCTG

AGAGATATGAGGGATATACAACCGTTGTCGTTAGAAAAACCTGCCGGCAA

AGTTGATTTAAAATTAATTGCATGTGAAGAGAAAAATAGTCAGGGAATGT

GTTCGTTAAAAAGTTTTTCCAGGCTCATTAAGGAAATTCGCGTGCCAGAG

TGTGCAGTTACGGAATAAGTAACTAATTACTATATATAGCGTATTAAAAA

ATAGAAACCCCCGGTTTGTAGTCGGGGGTATTCGTATTGTTCATAATTAC

A

SEQ ID No:3
MSTFIIRLLFFSLLCGSFSIHAEEPNGMKLERVVIVSRHGVRAPTKFTPI

MKDVTPDQWPQWDVPLGWLTPRGGELVSELGQYQRLWFTSKGLLNNQTCP

SPGQVAVIADTDQRTRKTGEAFLAGLAPKCQIQVHYQKDEEKTDPLFNPV

KMGTCSFNTLKVKNAILERAGGNIELYTQRYQSSFRTLENVLNFSQSETC

KTTEKSTKCTLPEALPSELKVTPDNVSLPGAWSLSSTLTEIFLLQEAQGM

PQVAWGRITGEKEWRDLLSLHNAQFDLLQRTPEVARSRATPLLDMIDTAL

LTNGTTENRYGIKLPVSLLFIAGHDTNLANLSGALDLNWSLPGQPDNTPP

GGELVFEKWKRTSDNTDWVQVSFVYQTLRDMRDIQPLSLEKPAGKVDLKL

IACEEKNSQGMCSLKSFSRLIKEIRVPECAVTE

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention will now be further described by the following numbered paragraphs:

1. An isolated polypeptide comprising the amino acid sequence corresponding to *Citrobacter freundii* phytase or a homologue, a modified form, a functional equivalent or an effective fragment thereof.

2. An isolated polypeptide as paragraphed in paragraph 1 comprising the amino acid sequence as shown in SEQ ID NO: 3 or a sequence having at least 75% identity (homology) thereto or a functional fragment thereof.

3. An isolated polypeptide having the amino acid sequence as set out in SEQ ID NO: 3 or a sequence having at least 75% identity (homology) thereto or a functional fragment thereof.

4. A phytase characterised in that it is derived from *Citrobacter freundii* strain P3-42 deposited under accession number NCIMB 41247.

5. A phytase or functional equivalent thereof characterised in that said phytase has a specific activity of at least 1100 U/mg wherein said specific activity is determined by incubating said phytase in a solution containing 2 mM phytate, 0.8 mM $CaCl_2$ in 200 mM sodium acetate buffer at pH 3.5.

6. A phytase or functional equivalent thereof characterised in that said phytase has two activity maxima around pH 3 and pH 4-4.5 wherein said activity is determined by incubating said phytase in a solution containing 2 mM phytate, 0.8 mM CaCl$_2$ in 200 mM sodium acetate buffer.

7. An isolated polypeptide or phytase as paragraphed in any of paragraphs 1 to 6 that comprises one or more mutations at the following positions (numbering according to the numbering in SEQ ID No. 3):
22, 23, 24, 28, 46, 53, 57, 67, 74, 75, 77, 78, 79, 82, 88, 95, 96, 97, 98, 101, 102, 103, 105, 109, 112, 122, 126, 136, 140, 142, 143, 148, 151, 152, 154, 156, 160, 161, 164, 168, 170, 176, 177, 195, 199, 203, 204, 205, 206, 207, 215, 224, 225, 229, 233, 235, 274, 279, 288, 301, 307, 308, 322, 343, 358, 360, 362, 365, 366, 367, 370, 383, 384, 385, 386, 391, 393, 395, 397, 408, 414.

8. An isolated polypeptide or phytase as paragraphed in paragraph 7 wherein said phytase comprises one or more of the following mutations: A22T, E23K, E23Q, E24D, M28L, K46E, K46R, D53K, D53N, D57Y, G67R, G74R, E75K, E75V, V77I, S78T, E79V, Q82H, Q82K, Q82R, F88Y, N95D, N95P, N96P, N96S, N96Y, Q97T, T98G, T98P, S101F, P102L, G103E, V105I, A109T, D112V, D112Y, F122Y, L126I, Y136N, E140V, K142R, T143I, T143P, N148D, K151G, M152K, M152V, T154I, S156T, L160F, K161N, N164D, E168D, A170T, L176Q, L176V, Y177F, S195T, T199I, T203I, T203L, T203S, T203W, E204A, E204G, E204H, E204I, E204N, E204R, E204V, K205P, K205R, S206R, S206T, T207A, T207S, L215F, D224H, N225D, N225E, P229S, S233C, S235A, Q274H, Q274L, Q279E, R288M, L301S, E307Y, N308D, N308T, A322V, G343A, K358R, K360N, T362A, T362I, N365D, T366S, D367N, Q370H, D383V, I384F, I384L, I384M, Q385R, P386Q, K391N, A393P, K395T, D397N, S408I, L414I.

9. An isolated polypeptide or phytase as paragraphed in paragraph 7 or paragraph 8 comprising one mutation selected from the group consisting of:
P229S; D112V; Q82R; Q274H; D112Y; F88Y; K46E; S233C; R288M; I384L; Q385R; Q274L; E307Y; T199I; Q82K and T203I.

10. An isolated polypeptide or phytase as paragraphed in paragraph 7 or 8 comprising a combination of mutations selected from the group consisting of:
K46E/Q82H; Q82K/V1O5I; N148D/T362I; K46E/L414I; F88Y/Y136N; T154I/P386Q; N95P/N96S; N95P/N96P; Q97T/T98G; D224H/N225E; Y177F/T199I; Q274L/Q370H; K46E/N96Y; N148D1L301S; E24D/R288M; E140V/A322V; K46E/S195T; E75K/N365D; T98P/S235A; L160F/L215F; Q274L/K395T; G67R/Q279E/N$_{208}$T; K161N/P229S/R288M; D53N/D57Y/M152V; F122Y/S156T/P229S; T199I/S206R/T207S; E23K/K46E/Q82H; K46E/Q82H/Q385R; T203W/E204N/K205R; T203W/E204H/K205R; T203W/E204R/K205R; T203W/E204A/K205R; A22T/K151G/N308D; E23K/E75K/F88Y; M152K/N225D/L301S; S78T/Q274L/S408I; L176Q/T199I/T366S; K46E/V77I/T203S; K46R/T199I/D367N; G74R/E204G/R288M; A22T/T199I/S206T/T207A; Q82R/F88Y/L126I/I384L; K46E/Q82H/E168D/Q274L; Q82K/T154I/Q279E/N308T; Q82R/D112V/Q274H/T362A; E24D/E79V/N95D/K360N; E23K/M28L/A109T/T143P/I384L; D53N/D57Y/T199I/P299S/R288M; K46E/Q82H/N148D/T154I/T362I; D53N/D57Y/P229S/R288M/K358R; D53N/D57Y/T154I/P229S/R288M; Y136N/T 199I/T203L/E204I/K205P; E23Q/S101F/Q274L/I384M/K391N; K46E/Q82H/N95D/D112V/K142R/D383V; D53N/D57Y/M 152V/P229S/R288M/A393P; D53K/D57Y/M 152V/P229S/R288M/A393P; D53N/D57Y/F88Y/M152V/P299S/Q279E/N308T; D53N/D57Y/M 152V/E204V/P229S/R288M/A393P; D53N/D57Y/M152V/T154I/P229S/R288M/A393P; D53N/D57Y/Q82H/G103E/M152V/P229S/R288M/A393P; K46E/D53N/D57Y/T143I/M152V/L176V/P229S/R288M/A393P; Q82K/F88Y/N96P/Q97T/T98G/V105I/Q274H/Q279E/A393P; Q82R/F88Y/N95P/N96P/Q97T/Q279E/1384L/P386Q/A393P; H18Q/D53N/D57Y/E75V/M152V/A170T/P229S/R288M/Q385R/A393P; Q82K/F88Y/N96P/T98G/Y136N/M152V/Y177F/T362I/I384F/A393P/D397N; D53N/D57Y/F88Y/N95P/N96P/V105I/D112V/Y136N/N148D/N164D/Q274H/T362I/I384L/A393P; D53N/D57Y/Q82K/F88Y/N95P/P102L/V105I/Y136N/N148D/Y177F/Q274H/Q279 E/T362I/A393P; D53N/D57Y/Q82K/F88Y/N96P/T98G/V105I/D112V/177F/Q274L/G343A/T362I/I384L/A393P.

11. An isolated nucleic acid molecule coding for the enzyme of *Citrobacter freundii* phytase, or a homologue thereof.

12. An isolated nucleic acid molecule as paragraphed in paragraph 11 encoding a polypeptide comprising the amino acid sequence as shown in SEQ ID NO: 3 or a sequence having at least 75% identity (homology) thereto or an effective fragment thereof.

13. An isolated nucleic acid molecule comprising a nucleotide sequence that is the same as, or is complementary to, or contains any suitable codon substitutions for any of those of SEQ ID NO: 2 or comprises a sequence which has at least 75%, 80%, 85%, 90%, 95% or 99% sequence homology with SEQ ID NO: 2.

14. An isolated nucleic acid molecule coding for the isolated polypeptide or phytase as paragraphed in any of paragraphs 1 to 10.

15. An isolated nucleic acid molecule comprising the sequence as set out in SEQ ID NO: 2.

16. A plasmid or vector system comprising an isolated polypeptide or phytase as paragraphed in any of paragraphs 1 to 10 or a homologue or derivative thereof.

17. A plasmid or vector system as paragraphed in paragraph 16 which comprises a nucleic acid sequence as paragraphed in any of paragraphs 11 to 15.

18. A plasmid or vector system as paragraphed in paragraph 16 which comprises a nucleic acid sequence as set out in SEQ ID No: 2 or a sequence that is at least 75% homologous thereto or an effective fragment thereof.

19. A plasmid or vector system as paragraphed in any of paragraphs 16 to 18 wherein said plasmid or vector system is an expression vector for the expression of the respective phytase enzyme or homologue, modified form, functional equivalent or effective fragment thereof, in a host cell or a microorganism.

20. A host cell transformed or transfected with a plasmid or vector system as paragraphed in any of paragraphs 16 to 19.

21. A host cell as paragraphed in paragraph 20 which comprises a phytase which comprises an amino acid sequence, or functional fragment thereof, as set out in SEQ ID NO: 3, or a sequence that is at least 75% homologous thereto, or a variant thereof according to any of paragraphs 7-10.

22. A host cell as paragraphed in paragraph 20 or 21 wherein said host cell is derived from a microorganism including bacteria, such as *B. subtilis, E. coli* and fungi, including yeast such as *H. polymorpha, S. pombe, S. cerevisiae.*

23. A host cell as paragraphed in paragraph 22 wherein said microorganism is a prokaryotic bacterial cell and, preferably, *E. coli.*

24. A bacterial cell strain *Citrobacter freundii* P3-42 deposited under accession number NCIMB 41247.

25. A method of producing a phytase comprising expressing an amino acid sequence as set out in SEQ ID NO: 3, or a sequence having at least 75% homology thereto or a modified form or a variant or an effective fragment thereof in a host cell and separating the phytase from the host cell culture medium.

26. A food or animal feed composition comprising a phytase as paragraphed in any of paragraphs 1 to 25.

27. Use of a phytase as paragraphed in any of paragraphs 1 to 10 in food or animal feed.

28. A method for production of food or animal feed comprising a step of spraying a phytase as paragraphed in any of paragraphs 1 to 10 in liquid form onto said food or animal feed.

29. A method for production of food or animal feed comprising a step of mixing the phytase as paragraphed in any of paragraphs 1 to 10 as a dry product with said food or animal feed.

30. A method of preparing a phytase enzyme variant, which method comprises:
 a) selecting a parent phytase enzyme, wherein the parent phytase enzyme is selected from:
  i. a parent phytase enzyme with at least 75% homology to SEQ ID No 3
  ii. a parent phytase enzyme derived from *Citrobacter* spp.
 b) making at least one alteration which is an insertion, a deletion or a substitution of an amino acid residue in the parent phytase enzyme to obtain a phytase enzyme variant
 c) screening for a phytase enzyme variant which compared to the parent phytase enzyme has:
  i. higher thermal stability and/or
  ii. specific activity and/or
  iii. proteolytic stability
 d) preparing the phytase enzyme variant.

31. A method of preparing a phytase enzyme variant, which method comprises:
 a) subjecting DNA sequence encoding a parent phytase enzyme to mutagenesis,
  wherein the parent phytase enzyme is selected from
  i. a parent phytase enzyme with at least 75% homology to SEQ ID No 3
  ii. a parent phytase enzyme derived from *Citrobacter* spp.
 b) expressing the mutated DNA sequence obtained in step (A) in a host cell, and
 c) screening for host cells expressing a phytase enzyme variant which compared to the parent phytase enzyme has:
  i. higher thermal stability and/or
  ii. higher specific activity and/or
  iii. higher proteolytic stability
 d) preparing the phytase enzyme variant expressed by the host cell.

The invention claimed is:

1. An isolated polypeptide comprising an amino acid sequence corresponding to *Citrobacter freundii* phytase, wherein the polypeptide has phytase activity and wherein the polypeptide comprises the amino acid sequence as shown in SEQ ID NO: 3 or a sequence having at least 90% identity thereto and wherein said polypeptide comprises the mutation R288M according to the numbering in SEQ ID NO:3.

2. An isolated phytase isolated from *Citrobacter freundii* strain P3-42, deposited under accession number NCIMB 41247.

3. The isolated polypeptide according to claim 1, having specific activity of at least 1100 U/mg, wherein said specific activity is determined by incubating said phytase in a solution containing 2 mM phytate, 0.8 mM CaCl$_2$ in 200 mM sodium acetate buffer at pH 3.5.

4. The isolated polypeptide according to claim 1, having two activity maxima around pH 3 and pH 4-4.5, wherein said activity is determined by incubating said phytase in a solution containing 2 mM phytate, 0.8 mM CaCl$_2$ in 200 mM sodium acetate buffer.

5. The isolated polypeptide according to claim 1, further comprising one or more of the following mutations selected from the group consisting of: P229S; D112V; Q82R; Q274H; D112Y; F88Y; K46E; S233C; I384L; Q385R; Q274L; E307Y; T199I; Q82K and T203I.

6. The isolated polypeptide according to claim 1, comprising a combination of mutations selected from the group consisting of: K46E/Q82H; Q82K/V105I; N148D/T362I; K46E/L414I; F88Y/Y136N; T154I/P386Q; N95P/N96S; N95P/N96P; Q97T/T98G; D224H/N225E; Y177F/T199I; Q274L/Q370H; K46E/N96Y; N148D/L301S; E24D/R288M; E140V/A322V; K46E/S195T; E75K/N365D; T98P/S235A; L160F/L215F; Q274L/K395T; G67R/Q279E/N208T; K161N/P229S/R288M; D53N/D57Y/M152V; F122Y/S156T/P229S; T199I/S206R/T207S; E23K/K46E/Q82H; K46E/Q82H/Q385R; T203W/E204N/K205R; T203W/E204H/K205R; T203W/E204R/K205R; T203W/E204A/K205R; A22T/K151G/N308D; E23K/E75K/F88Y; M152K/N225D/L301S; S78T/Q274L/S408I; L176Q/T199I/T366S; K46E/N77I/T203S; K46R/T199I/D367N; G74R/E204G/R288M; A22T/T199I/S206T/T207A; Q82R/F88Y/L126I/I384L; K46E/Q82H/E168D/Q274L; Q82K/T154I/Q279E/N308T; Q82R/D112V/Q274H/T362A; E24D/E79V/N95D/K360N; E23K/M28L/A109T/T143P/I384L; D53N/D57Y/T199I/P299S/R288M; K46E/Q82H/N148D/T154I/T362I; D53N/D57Y/P229S/R288M/K358R; D53N/D57Y/T154I/P229S/R288M; Y136N/T199I/T203L/E204I/K205P; E23Q/S101F/Q274L/I384M/K391N; K46E/Q82H/N95D/D112V/K142R/D383V; D53N/D57Y/M152V/P229S/R288M/A393P; D53K/D57Y/M152V/P229S/R288M/A393P; D53N/D57Y/F88Y/M152V/P299S/Q279E/N308T; D53N/D57Y/M152V/E204V/P229S/R288M/A393P; D53N/D57Y/M152V/T154I/P229S/R288M/A393P; D53N/D57Y/Q82H/G103E/M152V/P229S/R288M/A393P; K46E/D53N/D57Y/T143I/M152V/L176V/P229S/R288M/A393P; Q82K/F88Y/N96P/Q97T/T98G/V105I/Q274H/Q279E/A393P; Q82R/F88Y/N95P/N96P/Q97T/Q279E/I384L/P386Q/A393P; H18Q/D53N/D57Y/E75V/M152V/A170T/P229S/R288M/Q385R/A393P; Q82K/F88Y/N96P/T98G/

Y136N/M152V/Y177F/T362I/I384F/A393P/D397N; D53N/D57Y/F88Y/N95P/N96P/V 105I/D112V/Y136N/N148D/N164D/Q274H/T362I/I384L/A393P; D53N/D57Y/Q82K/F88Y/N95P/P102L/V 105I/Y136N/N148D/Y177F/Q274H/Q279E/T362I/A393P; D53N/D57Y/Q82K/F88Y/N96P/T98G/V105I/D112V/Y177F/Q274L/G343A/T362I/I384L/A393P.

7. A food or animal feed composition comprising the polypeptide as claimed in claim 1.

8. A method for production of food or animal feed comprising a step of spraying the polypeptide as claimed in claim 1 in liquid form onto said food or animal feed.

9. A method for production of food or animal feed comprising a step of mixing the polypeptide as claimed in claim 1 as a dry product with said food or animal feed.

10. The isolated polypeptide of claim 1 wherein said phytase further comprises one or more of the following mutations: A22T, E23K, E23Q, E24D, M28L, K46E, K46R, D53K, D53N, D57Y, G67R, G74R, E75K, E75V, V77I, S78T, E79V, Q82H, Q82K, Q82R, F88Y, N95D, N95P, N96P, N96S, N96Y, Q97T, T98G, T98P, S101F, P102L, G103E, V105I, A109T, D112V, D112Y, F122Y, L126I, Y136N, E140V, K142R, T143L, T143P, N148D, K151G, M152K, M152V, T154I, S156T, L160F, K161N, N164D, E168D, A170T, L176Q, L176V, Y177F, S195T, T199I, T203I, T203L, T203S, T203W, E204A, E204G, E204H, E204I, E204N, E204R, E204V, K205P, K205R, S206R, S206T, T207A, T207S, L215F, D224H, N225D, N225E, P229S, S233C, S235A, Q274H, Q274L, Q279E, L301S, E307Y, N308D, N308T, A322V, G343A, K358R, K360N, T362A, T362I, N365D, T366S, D367N, Q370H, D383V, I384F, I384L, I384M, Q385R, P386Q, K391N, A393P, K395T, D397N, S408I, L414I.

* * * * *